United States Patent [19]

Michalczyk et al.

[11] Patent Number: 5,378,790
[45] Date of Patent: Jan. 3, 1995

[54] SINGLE COMPONENT INORGANIC/ORGANIC NETWORK MATERIALS AND PRECURSORS THEREOF

[75] Inventors: Michael J. Michalczyk, Wilmington, Del.; Kenneth G. Sharp, Landenburg, Pa.

[73] Assignee: E. I. Du Pont de Nemours & Co., Wilmington, Del.

[21] Appl. No.: 120,995

[22] Filed: Sep. 13, 1993

Related U.S. Application Data

[63] Continuation-in-part of Ser. No. 945,777, Sep. 16, 1992, abandoned.

[51] Int. Cl.$^6$ .............................................. C08G 77/60
[52] U.S. Cl. ........................................ 528/35; 528/12; 528/25; 528/34; 427/387
[58] Field of Search .................... 528/35, 12, 25, 34, 528/39; 427/387

[56] References Cited

U.S. PATENT DOCUMENTS

| | | | |
|---|---|---|---|
| 3,159,662 | 12/1964 | Ashby | 260/448.2 |
| 3,220,972 | 11/1965 | Lamoreaux | 260/46.5 |
| 3,271,362 | 9/1966 | Chalk et al. | 260/46.5 |
| 3,542,830 | 11/1970 | Kim et al. | 260/448.2 |
| 4,221,691 | 9/1980 | Danielson et al. | 260/33.6 |
| 4,461,867 | 7/1984 | Surprenant | 524/788 |
| 4,513,132 | 4/1985 | Shoji et al. | 528/21 |
| 4,689,085 | 8/1987 | Plueddemann | 106/287 |
| 4,775,415 | 10/1988 | Mohr et al. | 106/14.05 |
| 5,145,907 | 9/1992 | Kalinowski et al. | 524/789 |
| 5,202,404 | 4/1993 | Takarada et al. | 528/34 |

FOREIGN PATENT DOCUMENTS

| | | | |
|---|---|---|---|
| 2067435 | 10/1992 | Canada | B32B 27/8 |
| 0183533 | 6/1986 | European Pat. Off. | C08G 77/16 |
| 0409272 | 1/1991 | European Pat. Off. | C09J 183/06 |
| 0496597 | 7/1992 | European Pat. Off. | C07F 7/08 |
| 2008426 | 9/1970 | Germany | C08G 31/34 |
| 1966503 | 3/1973 | Germany . | |
| 914580 | 3/1982 | U.S.S.R. | C08G 77/18 |
| WO90/15098 | 12/1990 | WIPO | C07F 7/2 |

OTHER PUBLICATIONS

Ousgi, K. et al, *Chemical Abstracts*, 115(20), Nov. 18, 1991, Abstract No. 210341f, p. 127.
Ona, I. et al, *Chemical Abstracts*, 108(10), Mar. 7, 1988, Abstract No. 76116m, p. 17.
Lewis, L. N. et al, *Chemical Abstracts*, 110(8), Feb. 10, 1989, Abstract No. 64253g, p. 436.
Gorshkov, A. V. et al, *Chemical Abstracts*, 110(20), May 15, 1989, Abstract No. 174875u, p. 81.
Birkofer, L. et al, *Journal of Organometallic Chemistry*, 299, 143–148, 1986.
Kagawa, H. et al, *Chemical Abstracts*, 116(6), Feb. 10, 1992, Abstract No. 42881g, p. 63.
Kim et al., The Synthesis of $\alpha,\psi$-Bis-(Silyl)Polyfluoroalkane Derivatives, *J. Fluorine Chem.*, 1, 203–218, 1971/72.
van der Made et al., Silane Dendrimers, *J. Chem. Soc., Chem. Commun.*, 1400–1401, 1992.
Corriu et al., New Mixed Organic–Inorganic Polymers: Hydrolysis and Polycondensation of Bis(trimethoxysilyl)organometallic Precursors, *Chem. Mater.*, 4, 1217–1224, 1992.
Shea et al., Aryl-Bridged Polysilsesquioxanes–New Microporous Materials, *Chemistry of Materials*, 1, 572–574, 1989.
Oviatt et al., Alkylene–Bridged Silsesquioxane Sol–Gel Synthesis and Xerogel Characterization, *Chemistry of Materials*, 5, 943, 1993.

(List continued on next page.)

*Primary Examiner*—Melvyn I. Marquis

[57] ABSTRACT

Single component inorganic/organic network materials incorporating the physical properties of glasses with the flexibility of organic materials of empirical formula $X(SiO_{1.5})_n$ wherein X is one or more flexible organic linkages and n is greater than or equal to 2, as well as precursors thereof, are disclosed.

5 Claims, No Drawings

OTHER PUBLICATIONS

Glaser et al., Solid-State $^{29}$Si NMR of TEOS-Based Multifunctional Sol-Gel Materials, *J. Non-Cryst. Solids*, 113, 73–87, 1989.

Michel et al., No. 701.—Synthese, proprietes spectroscopiques IR et RMN et viscosimetrie de quelques p-phenylene disilanes substitues., *Bull. Soc. Chim. Fr.*, 11, 4107–4116, 1971.

Hadjichristidis et al., Star-Branched Polymers. 1. The Synthesis of Star Polyisoprenes using Octa- and Dodecachlorosilanes as Linking Agents, *Macromolecules*, 11 (4), 668–672, 1978.

Hadjichristidis et al., Star-Branched Polymers. 4. Synthesis of 18-Arm Polyisoprenes, *Macromolecules*, 13, 191–193, 1990.

Burch, Oxidation-Reduced Reactions for Preparation of $[Ti(OC_6H_4O)_2]_n$ and Related Metalloquinone Polymers: Hybrid Inorganic-Organic Metal Oxides, *Chem. Mater.*, 2 (6), 633–635, 1990.

Webster et al., Hypercrosslinked Rigid-Rod Polymers, *Makromol. Chem., Macromol. Symp.*, 54/55, 477–482, 1992.

Mathias et al., Hyperbranched and Star Poly(siloxysilanes) via Polymerization of A-B$_3$ and A-B Monomers, *Polm. Prepr. (Am. Chem. Soc., Div. Polym. Chem.)*, 32, 35–37, 1992.

Stivala et al., Small-angle X-ray Scattering from 12-Arm Star Polystyrene Fractions in MEK, *Polymer*, 27, 517–522, 1986.

Guyot, Silicon Chemistry and Cationic Polymerization, *Polym. Prepr. (Am. Chem. Soc., Div. Polym. Chem.)*, 26 (1), 46–47, 1985.

SINGLE COMPONENT INORGANIC/ORGANIC NETWORK MATERIALS AND PRECURSORS THEREOF

This is a continuation-in-part of application Ser. No. 07/945,777 filed Sep. 16, 1992, now abandoned.

This invention concerns single component inorganic/organic materials which consist essentially of a multi-component network comprising flexible organic and rigid inorganic portions.

A significant limitation on both the generation and utility of inorganic network materials such as glasses and ceramics relates to their brittleness. When glasses are prepared at room temperatures using sol-gel technology, Brinker, C. J., et al., Sol Gel Science, Academic Press, San Diego, Calif. (1990) drying stresses cause catastrophic fracture of films more than about 0.5 micron in thickness (for fully dense silica); larger monolithic structures are possible only with low drying rates. Applications for inorganic glasses are limited to those in which considerable amounts of energy absorption or dissipation (i.e., toughness) are not required.

Prior attempts to make the glass network more compliant have involved limiting the number of networking bonds per silicon atom (e.g., using alkyl(trialkoxy) silanes instead of tetraalkoxy silanes). There is growing interest in inorganic/organic hybrid materials which incorporate both glasses and flexible organic material. One approach has been to incorporate organic polymers into silica glasses.

K. J. Shea et al., Chemistry of Materials, 1, 572(1989), disclose organically modified silicates prepared by sol-gel processing of bis-triethoxysilylaryl and bis-trichlorosilylaryl monomers. The three monomers employed had the aryl portion of the monomer as phenylene ($-C_6H_4-$), biphenylene ($-C_6H_4-C_6H_4-$), and triphenylene ($-C_6H_4-C_6H_4-C_6H_4-$). Rigid networks are produced which are brittle, porous and contain a single rigid organic link between silicon atoms.

The present invention comprises a new class of network materials which incorporate both glasses and flexible organic materials without suffering the deficiencies of the glasses produced by conventional sol-gel technology. This invention concerns certain compositions having chemically bonded inorganic network portions and organic network portions. These two portions may be derived from a single precursor molecule or from a mixture of precursor molecules, which precursor molecules contain the elements of, or precursors to the elements of, both the inorganic and organic portions. Because both the organic and inorganic portions of the composition derive from the same precursor molecule, or from a mixture of such precursor molecules, the portions cannot be separated without the breaking of chemical bonds.

SUMMARY OF THE INVENTION

This invention comprises an inorganic/organic composition of the idealized empirical formula (II):

$$X(SiO_{1.5})_n \qquad (II)$$

wherein
  n is an integer greater than or equal to 2; and
  X is at least one flexible organic link selected from the group consisting of:
  (a) $R^1{}_mSiY_{4-m}$;
  (b) ring structures

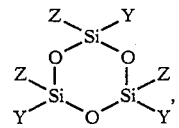
IIa

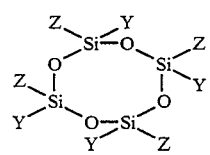
IIb and

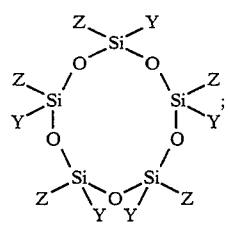
IIc (c) $R^1{}_mSi(OSi(CH_3)_2Y)_{4-m}$;
  (d) $R^1{}_mSi(OY)_{4-m}$;
  (e) $CH_3SiY_2-O-SiY_2CH_3$;
  (f) $Y(CH_3)_2Si-C_6H_4-Si(CH_3)_2Y$;
  (g) $O[-C_6H_4-Si(CH_3)_2Y]_2$;
  (h) $O[Si(CH_3)_2Y]_2$;
  (i) $Y(CH_3)_2SiCH_2-CH_2Si(CH_3)_2Y$;
  (j) $Y(CF_2)_pY$, provided that when p is 6, Y is other than ethylene;
  (k) $Y_3SiOSiY_3$;
  (l) $Y_3Si(CH_2)_bSiY_3$; and
  (m) $Y_3SiC_6H_4SiY_3$;
  (n) substituted benzene, including all isomers, selected from the group consisting of:
    (i) $C_6H_3(SiZ_{3-a}Y_a)_3$;
    (ii) $C_6H_2(SiZ_{3-a}Y_a)_4$;
    (iii) $C_6H(SiZ_{3-a}Y_a)_5$; and
    (iv) $C_6(SiZ_{3-a}Y_a)_6$; and
  (o) substituted cyclohexane, including all stereoisomers, selected from the group consisting of:
    (i) $1,2-C_6H_{10}(Y)_2$; $1,3-C_6H_{10}(Y)_2$; $1,4-C_6H_{10}(Y)_2$
    (ii) $1,2,4-C_6H_9(Y)_3$; $1,2,3-C_6H_9(Y)_3$; $1,3,5-C_6H_9(Y)_3$;
    (iii) $1,2,3,4-C_6H_8(Y)_4$; $1,2,4,5-C_6H_8(Y)_4$; $1,2,3,5-C_6H_8(Y)_4$;
    (iv) $1,2,3,4,5-C_6H_7(Y)_5$; and
    (v) $C_6H_6(Y)_6$;

wherein:
  Z is an alkyl group of 1 to 4 carbon atoms, 3,3,3-trifluoropropyl, aralkyl, or aryl;
  Y is $(CR^2R^3)_kCR^4R^5CR^6R^7(CR^8R^9)_h-$;
  $R^1$ is alkyl of 1 to about 8 carbon atoms or aryl;
  $R^2$ to $R^9$ are each independently hydrogen, alkyl of 1 to about 8 carbon atoms or aryl, provided that at least one of $R^4$ to $R^7$ is hydrogen;
  m is 0, 1 or 2;

k and h are each independently an integer from 0 to 10, provided that at least one of k or h is zero;
a is 1, 2 or 3;
p is an even integer from 4 to 10; and
b is an integer from 1 to 10.

This invention also comprises:
a compound of the formula (I):

$$X(SiQ_3)_n \qquad (I)$$

wherein:
Q is alkoxy of 1 to about 8 carbon atoms, acyloxy of 1 to about 8 carbon atoms, or halogen;
n is an integer greater than or equal to 2; and
X is at least one flexible organic link selected from the group consisting of:
(a) $R^1_m SiY_{4-m}$;
(b) ring structures

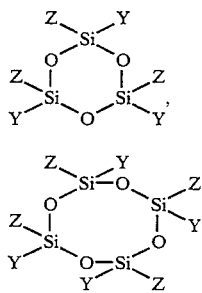

Ia

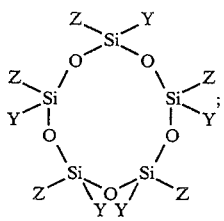

Ib and

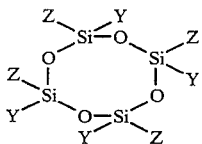

Ic provided that when X is

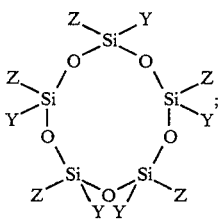

Ib

Z is other than methyl and Y is other than ethylene or propylene; and when X is

Ic

Z is other than methyl and Y is other than ethylene or propylene;

(c) $R^1_m Si(OSi(CH_3)_2Y)_{4-m}$;
(d) $R^1_m Si(OY)_{4-m}$;
(e) $CH_3SiY_2-O-SiY_2CH_3$;
(f) $Y(CH_3)_2Si-C_6H_4-Si(CH_3)_2Y$; provided that in the definition of Y as defined below either h or k is greater than zero when Q is ethoxy;
(g) $O[-C_6H_4-Si(CH_3)_2Y]_2$;
(h) $O[Si(CH_3)_2(Y)]_2$; provided that in the definition of Y as defined below either h or k is greater than zero when Q is ethoxy;
(i) $Y(CH_3)_2SiCH_2-CH_2Si(CH_3)_2Y$;
(j) $Y(CF_2)_pY$, provided that Y is other than ethylene;
(k) $Y_3SiOSiY_3$;
(l) $Y_3Si(CH_2)_bSiY_3$;
(m) $Y_3SiC_6H_4SiY_3$;
(n) substituted benzene, including all isomers, selected from the group consisting of:
 (i) $C_6H_3(SiZ_{3-a}Y_a)_3$;
 (ii) $C_6H_2(SiZ_{3-a}Y_a)_4$;
 (iii) $C_6H(SiZ_{3-a}Y_a)_5$; and
 (iv) $C_6(SiZ_{3-a}Y_a)_6$; and
(o) substituted cyclohexane, including all stereoisomers, selected from the group consisting of:
 (i) $1,2-C_6H_{10}(Y)_2$; $1,3-C_6H_{10}(Y)_2$; $1,4-C_6H_{10}(Y)_2$;
 (ii) $1,2,4-C_6H_9(Y)_3$; $1,2,3-C_6H_9(Y)_3$; $1,3,5-C_6H_9(Y)_3$;
 (iii) $1,2,3,4-C_6H_8(Y)_4$; $1,2,4,5-C_6H_8(Y)_4$; $1,2,3,5-C_6H_8(Y)_4$;
 (iv) $1,2,3,4,5-C_6H_7(Y)_5$; and
 (v) $C_6H_6(Y)_6$;

wherein:
Z is an alkyl group of 1 to 4 carbon atoms, 3,3,3-trifluoropropyl, aralkyl or aryl;
Y is $(CR^2R^3)_k CR^4R^5CR^6R^7(CR^8R^9)_h-$;
$R^1$ is alkyl of 1 to about 8 carbon atoms or aryl;
$R^2$ to $R^9$ are each independently hydrogen, alkyl of 1 to about 8 carbon atoms or aryl, provided that at least one of $R^4$ to $R^7$ is hydrogen;
m is 0, 1 or 2;
k and h are each independently an integer from 0 to 10, provided that at least one of k or h is zero;
a is 1, 2 or 3;
p is an even integer from 4 to 10; and
b is an integer from 1 to 10.

This invention further comprises a compound of the formula III(j)':

$$(SiQ_3)_n CH_2CH_2(CF_2)_p CH_2CH_2(SiQ_3)_n \qquad III(j)'$$

wherein:
Q is alkoxy of 1 to about 8 carbon atoms, acyloxy of 1 to about 8 carbon atoms, or halogen;
n is an integer greater than or equal to 2;
and p is an even integer from 4 to 10.

This invention further comprises a process for the preparation of a compound of formula (I), $X(SiQ_3)_n$, as defined above comprising reacting a compound containing an Si-H group with a compound containing an olefinic or alkynyl bond in the presence of a transition metal catalyst such as platinum, or a free-radical initiator.

This invention further comprises a method for modifying sol-gel glasses comprising:

(a) combining a star gel precursor compound of formula (III), X (SiQ$_3$)$_n$ wherein Q is alkoxy of 1 to about 8 carbon atoms, acyloxy of 1 to about 8 carbon atoms, or halogen;

n is an integer greater than or equal to 2; and

X is at least one flexible organic link selected from the group consisting of:
(a) R$^1_m$SiY$_{4-m}$;
(b) ring structures

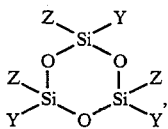
IIIa

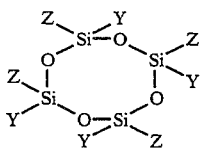
IIIb and

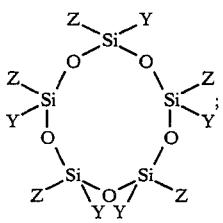
IIIc (c) R$^1_m$Si(OSi(CH$_3$)$_2$Y)$_{4-m}$;
(d) R$^1_m$Si(OY)$_{4-m}$;
(e) CH$_3$SiY$_2$—O—SiY$_2$CH$_3$;
(f) Y(CH$_3$)$_2$Si—C$_6$H$_4$—Si(CH$_3$)$_2$Y;
(g) O[—C$_6$H$_4$—Si(CH$_3$)$_2$Y]$_2$;
(h) O[Si(CH$_3$)$_2$Y]$_2$;
(i) Y(CH$_3$)$_2$SiCH$_2$—CH$_2$Si(CH$_3$)$_2$Y;
(j) Y(CF$_2$)$_p$Y;
(k) Y$_3$SiOSiY$_3$;
(l) Y$_3$Si(CH$_2$)$_b$SiY$_3$; and
(m) Y$_3$SiC$_6$H$_4$SiY$_3$;
(n) substituted benzene, including all isomers, selected from the group consisting of:
 (i) C$_6$H$_3$(SiZ$_{3-a}$Y$_a$)$_3$;
 (ii) C$_6$H$_2$(SiZ$_{3-a}$Y$_a$)$_4$;
 (iii) C$_6$H(SiZ$_{3-a}$Y$_a$)$_5$; and
 (iv) C$_6$(SiZ$_{3-a}$Y$_a$)$_6$; and
(o) substituted cyclohexane, including all stereoisomers, selected from the group consisting of:
 (i) 1,2-C$_6$H$_{10}$(Y)$_2$; 1,3-C$_6$H$_{10}$(Y)$_2$; 1,4-C$_6$H$_{10}$(Y)$_2$;
 (ii) 1,2,4-C$_6$H$_9$(Y)$_3$; 1,2,3-C$_6$H$_9$(Y)$_3$; 1,3,5-C$_6$H$_9$(Y)$_3$;
 (iii) 1,2,3,4-C$_6$H$_8$(Y)$_4$; 1,2,4,5-C$_6$H$_8$(Y)$_4$; 1,2,3,5-C$_6$H$_8$(Y)$_4$;
 (iv) 1,2,3,4,5-C$_6$H$_7$(Y)$_5$; and
 (v) C$_6$H$_6$(Y)$_6$;

wherein:

Z is an alkyl group of 1 to 4 carbon atoms, 3,3,3-trifluoropropyl, aralkyl, or aryl;

Y is (CR$^2$R$^3$)$_k$CR$^4$R$^5$CR$^6$R$^7$(CR$^8$R$^9$)$_h$—;

R$^1$ is alkyl of 1 to about 8 carbon atoms or aryl;

R$^2$ to R$^9$ are each independently hydrogen, alkyl of 1 to about 8 carbon atoms or aryl, provided that at least one of R$^4$ to R$^7$ is hydrogen;

m is 0, 1 or 2;

k and h are each independently an integer from 0 to 10, provided that at least one of k or h is zero;

a is 1, 2 or 3;

p is an even integer from 4 to 10; and b is an integer from 1 to 10;

with a metal alkoxide sol-gel precursor;

(b) mixing in water with a solvent and a catalyst or a carboxylic acid optionally in the presence of a solvent; and (c) drying.

The resulting modified sol-gel glass can tolerate increased drying rates and shows lower brittleness compared to the corresponding unmodified sol-gel glass.

This invention further comprises a process for the preparation of the composition of formula (II) as defined above comprising:

(a) mixing at least one compound of formula (I) or formula (III) as defined above with water in the presence of a solvent and a catalyst, or with at least one strong carboxylic acid having a pKa value of a maximum of about 4.0 and containing from 0 to 20 mole % water;

(b) maintaining the mixture resulting from step (a) at a temperature within the range of about 0°–100° C.; and (c) isolating the resulting inorganic/organic composition of formula (II).

This invention further comprises a method for coating a substrate comprising reacting the star gel precursor of formula (III), as defined above, with water in the presence of a solvent and a catalyst, or a strong carboxylic acid optionally in the presence of a solvent, dipping the substrate in the resulting mixture, removing the coated substrate from the mixture, and drying the coating to generate a substrate coated with a composition of formula II, as defined above.

DETAILED DESCRIPTION OF THE INVENTION

This invention provides certain inorganic/organic compositions comprising inorganic network portions and organic network portions. These two portions are derived from a single precursor molecule, or from a mixture of precursor molecules, which precursor molecules contain the elements of, or precursors to the elements of, both the inorganic and organic portions. Because both the organic and inorganic portions of the composition derive from the same precursor molecule, or from a mixture of such precursor molecules, the composition cannot be separated without the breaking of chemical bonds.

The present invention further comprises a method for modifying conventional sol-gel glasses to increase drying rates and lower brittleness comprising combining a star gel precursor of the present invention of formula (I) or formula (III) with a conventional sol-gel system based on tetraalkoxysilanes or other metal alkoxides; mixing in water with a solvent and a catalyst, or a carboxylic acid optionally in the presence of a solvent; and drying.

The inorganic/organic network compositions of the present invention, which can be in the form of gels or glasses, are of the idealized empirical formula (II):

$$X(SiO_{1.5})_n \qquad (II)$$

as defined above wherein X is one or more flexible organic links, which simultaneously interconnect n silicon atoms where n is an integer greater than or equal to 2. Each of the latter atoms will be constituents of a network structure via bonds to other silicon atoms through oxygen. For example, an inorganic/organic gel formed from Star 1 (claim 1, (a)) which is $X(SiO_{1.5})_n$ wherein $X=Si(CH_2CH_2-)_4$, $Y=-CH_2CH_2-$, $m=0$ and $n=4$ and the Si's of the Si—O—Si crosslinks are shown in standard print and the Si's of X in italics, could be represented as follows:

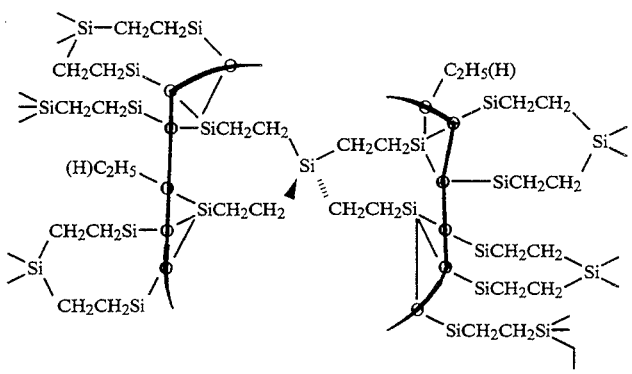

Condensation to form Si—O—Si cross links from Si—OC₂H₅ by hydrolysis does not go to 100% completion; this is shown above by residual, uncrosslinked SiOC₂H₅ or SiOH groups. An idealized formula corresponds to 100% crosslinking. The idealized empirical formula of the inorganic/organic gel derived from Star 1 as shown above would be: $Si(CH_2CH_2SiO_{1.5})_4$— the unit within the two half circles which bisect the oxygen atoms.

The number of $SiO_{1.5}$ groups depend on the number of Y's as defined in formula (I), (II) or (III). On the average there are 1.5 oxygens associated with each Si. For example, when there are two Y's there are 2 Si's. Every Y is attached to a Si; there are no unsatisfied valences. There will be —OR or —OH groups that are not crosslinked which is desirable on the perimeter of the network for reacting with components in other compositions.

These compositions are prepared by the hydrolysis of one or more star gel precursors of the present invention of formula (I) or formula (III). Star gel precursors are molecules which comprise a flexible organic or inorganic core comprising a central atom, ring or short linear segment linked to multiple arms which terminate in a silicon atom which bears at least two hydrolyzable substituents. The star gel precursors of the present invention comprise compounds of formula (I)

$$x(SiQ_3)_n \qquad (I)$$

wherein X is at least one flexible organic link, as defined below, n is an integer greater than or equal to 2, and Q is a hydrolyzable group such as alkoxy containing from 1 to about 8 carbon atoms, acyloxy of 1 to about 8 carbon atoms, or halogen.

In general for formula (I), X comprises a central atom, ring or short linear segment with a number of arms which terminate in a silicon atom. In particular X comprises one or more flexible organic links selected from the group consisting of:

(a) $R^1{}_m SiY_{4-m}$;
(b) ring structures

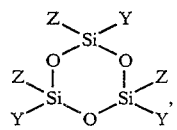 Ia

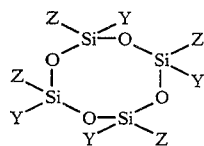 Ib and

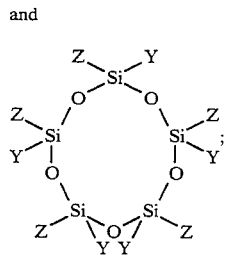 Ic provided that when X is

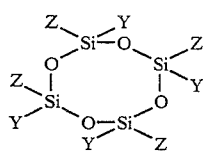 Ib

Z is other than methyl and Y is other than ethylene or propylene; and when X is

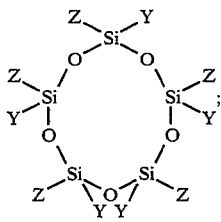

Z is other than methyl and Y is other than ethylene or propylene;

(c) $R^1_mSi(OSi(CH_3)_2Y)_{4-m}$;

(d) $R^1_mSi(OY)_{4-m}$;

(e) $CH_3SiY_2$—O—$SiY_2CH_3$;

(f) $Y(CH_3)_2Si$—$C_6H_4$—$Si(CH_3)_2Y$; provided that in the definition of Y as defined below either h or k is greater than zero when Q is ethoxy;

(g) $O[$—$C_6H_4$—$Si(CH_3)_2Y]_2$;

(h) $O[Si(CH_3)_2Y]_2$; provided that in the definition of Y as defined below either h or k is greater than zero when Q is ethoxy;

(i) $Y(CH_3)_2SiCH_2$—$CH_2Si(CH_3)_2Y$;

(j) $Y(CF_2)_pY$, provided that Y is other than ethylene;

(k) $Y_3SiOSiY_3$;

(l) $Y_3Si(CH_2)_bSiY_3$;

(m) $Y_3SiC_6H_4SiY_3$;

(n) substituted benzene, including all isomers selected from the group consisting of:
 (i) $C_6H_3(SiZ_{3-a}Y_a)_3$;
 (ii) $C_6H_2(SiZ_{3-a}Y_a)_4$;
 (iii) $C_6H(SiZ_{3-a}Y_a)_5$; and
 (iv) $C_6(SiZ_{3-a}Y_a)_6$; and (o) substituted cyclohexane, including all stereoisomers, selected from the group consisting of:
 (i) $1,2$-$C_6H_{10}(Y)_2$; $1,3$-$C_6H_{10}(Y)_2$; $1,4$-$C_6H_{10}(Y)_2$;
 (ii) $1,2,4$-$C_6H_9(Y)_3$; $1,2,3$-$C_6H_9(Y)_3$; $1,3,5$-$C_6H_9(Y)_3$;
 (iii) $1,2,3,4$-$C_6H_8(Y)_4$; $1,2,4,5$-$C_6H_8(Y)_4$; $1,2,3,5$-$C_6H_8(Y)_4$;
 (iv) $1,2,3,4,5$-$C_6H_7(Y)_5$; and
 (v) $C_6H_6(Y)_6$;

wherein:

Z is an alkyl group of 1 to 4 carbon atoms, 3,3,3-trifluoropropyl, aralkyl or aryl;

Y is $(CR^2R^3)_kCR^4R^5CR^6R^7(CR^8R^9)_h$—;

$R^1$ is alkyl of 1 to about 8 carbon atoms or aryl;

$R^2$ to $R^9$ are each independently hydrogen, alkyl of 1 to about 8 carbon atoms or aryl, provided that at least one of $R^4$ to $R^7$ is hydrogen;

m is 0, 1 or 2;

k and h are each independently an integer from 0 to 10, provided that at least one of k or h is zero;

a is 1, 2 or 3;

p is an even integer from 4 to 10; and b is an integer from 1 to 10.

For formula (I), (II) and (III) the most preferred flexible organic link, X, is where m is 0, k is 0 or 1, h is 0 or 1, and all of $R^2$ to $R^9$ are hydrogen. The preferred Q are alkoxy of 1 to about 3 carbon atoms. Most preferred Q is ethoxy. The most preferred halogen is chloro. The preferred aralkyl is benzyl. The preferred aryl is phenyl.

Preferred star gel precursors of formula III include those listed in Table I below.

TABLE I

| Star-Gel Precursors | |
|---|---|
| Star 1: | $Si(CH_2CH_2Si(OC_2H_5)_3)_4$ |
| Star 2: | 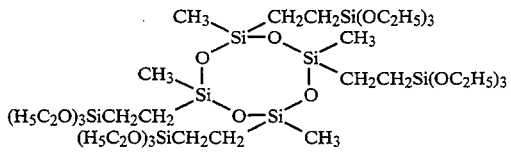 |
| Star 3: | $Si[OSi(CH_3)_2CH_2CH_2Si(OC_2H_5)_3]_4$ |
| Star 4: | $Si(OCH_2CH_2CH_2Si(OC_2H_5)_3)_4$ |
| Star 5: | 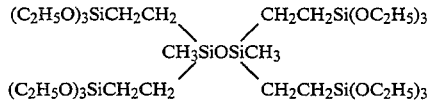 |
| Star 6: | 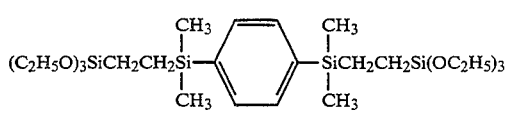 |
| Star 7: | 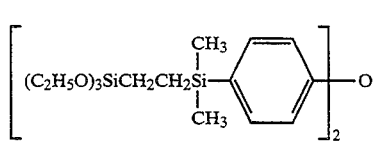 |

TABLE I-continued

Star-Gel Precursors

Star 8:

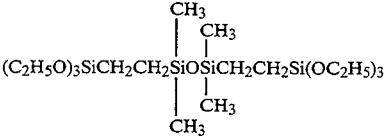

(C₂H₅O)₃SiCH₂CH₂Si(CH₃)(OCH₃)(CH₃)OSiCH₂CH₂Si(OC₂H₅)₃

Star 9:

(C₂H₅O)₃SiCH₂CH₂Si(CH₃)(CH₃)CH₂CH₂Si(CH₃)(CH₃)CH₂CH₂Si(OC₂H₅)₃

Star 10:

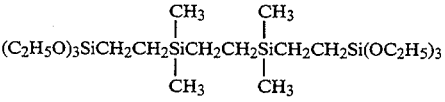

Star 11: Si(CH₂CH₂CH₂Si(OC₂H₅)₃)₄

Star 12:

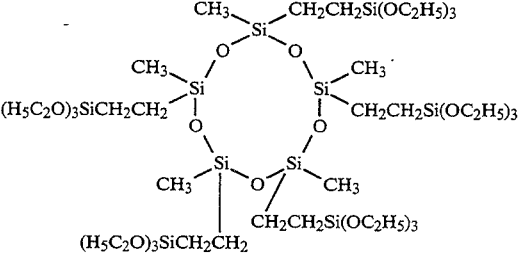

Star 13:

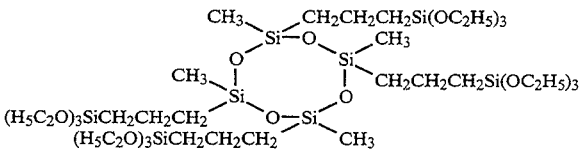

Star 14: Si[OSi(CH₃)₂CH₂CH₂CH₂Si(OC₂H₅)₃]₄

Star 15:

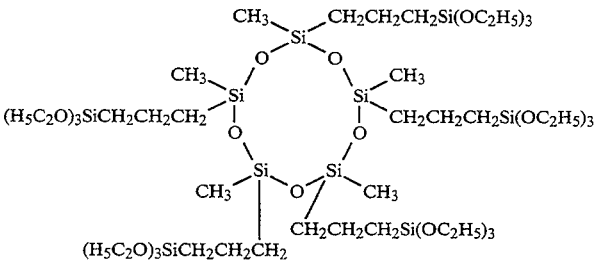

Star 16: (C₂H₅O)₃SiCH₂CH₂(CF₂)$_p$CH₂CH₂Si(OCH₂H₅)₃
Star 17: CH₃Si[OSi(CH₃)₂CH₂CH₂Si(OCH₂H₅)₃]₃
Star 18: Si[CH₂CH₂Si(OCH₃)₃]₄

Star 19:

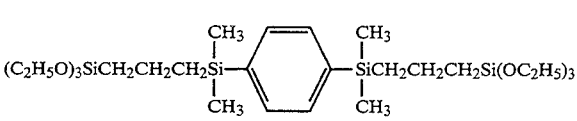

Star 20:

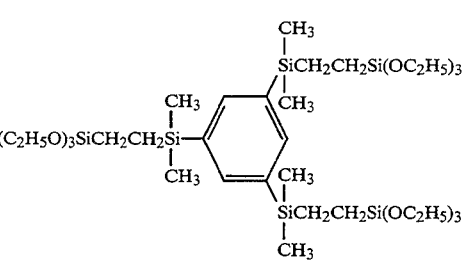

TABLE I-continued

Star-Gel Precursors

Star 21: $(C_2H_5O)_3Si(CH_2)_6(CF_2)_{10}(CH_2)_6Si(OC_2H_5)_3$

Star 22:

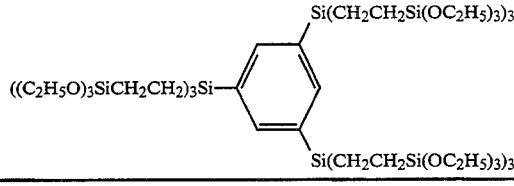

Preferred star gel precursors of formula I include Stars 1, 3, 4, 5, 7, 9, 11, 13, 14, 15, 17, 18, 19, 20, 21, and 22 as shown in Table I.

The present invention also comprises a compound of the formula III(j)':

$$(SiQ_3)_nCH_2CH_2(CF_2)_pCH_2CH_2(SiQ_3)_n \quad \text{III(j)'}$$

wherein:
Q is alkoxy of 1 to about 8 carbon atoms, acyloxy of 1 to about 8 carbon atoms, or halogen;
n is an integer greater than or equal to 2; and
p is an even integer from 4 to 10.

Q is preferably ethoxy or $C_1$. p is preferably 6 or 10.

The present invention further comprises processes for preparation of star gel precursors of formula I as defined above.

Synthesis of the star gel precursors is afforded from hydrosilylation reactions, i.e. an addition reaction between a compound containing a Si-H group with a compound containing aliphatic unsaturation (C=C or —C≡C—) in the presence of a catalyst or free radical initiator. Precursor segments containing —CH=CH$_2$ groups react with other precursor segments which contain terminal Si-H bonds. With these precursor segments a number of different flexible star gel precursors can be constructed as illustrated in Table 1.

Either precursor segment may contain the vinyl or other unsaturated group capable of Si-H addition. For example, $Si(CH=CH_2)_4$ reacts with $HSi(OC_2H_5)_3$ to form star gel precursor 1, $Si[CH_2CH_2Si(OC_2H_5)_3]_4$; and cyclo[(CH$_3$)HSiO]$_5$ reacts with $CH_2=CH-Si(OC_2H_5)_3$ to form star gel precursor 10, cyclo $[OSi(CH_3)CH_2CH_2Si(OC_2H_5)_3]_5$.

All of the following equations with the exception of Equations 7B and 7C provide for preparation of compounds of formula I by addition of a silane across a carbon-carbon double bond for various definitions of X:

(a) when X is $R^1{}_mSi[Y]_{4-m}$:

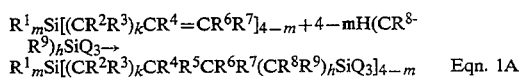

Eqn. 1A or

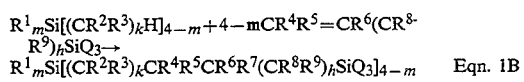

Eqn. 1B (b) when X is a ring structure of the type Ia, Ib or Ic as previously defined which can be abbreviated (Si-O)$_u$Z$_u$(YSiQ$_3$)$_u$, wherein u=3 for Ia, u=4 for Ib, and u=5 for Ic; then

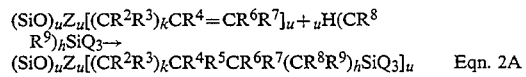

Eqn. 2A

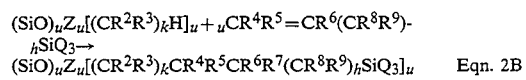

Eqn. 2B (c) when X is $R^1{}_mSi[OSi(CH_3)_2Y]_{4-m}$:

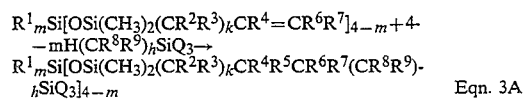

Eqn. 3A or

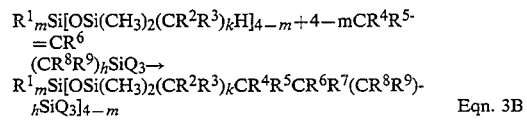

Eqn. 3B (d) when X is $R^1{}_mSi[OY]_{4-m}$:

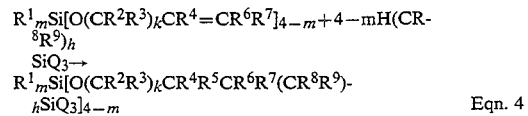

Eqn. 4

(e) when X is $CH_3SiY_2$—O—$SiY_2CH_3$:

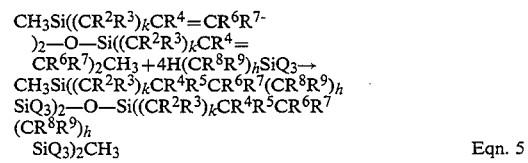

Eqn. 5 or

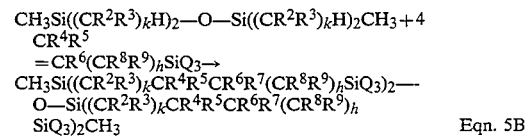

Eqn. 5B when X is
(f) $Y(CH_3)_2Si$—$C_6H_4$—$Si(CH_3)_2Y$;
(g) $O[-C_6H_4-Si(CH_3)_2Y]_2$;
(h) $O[Si(CH_3)_2Y]_2$; or
(i) $Y(CH_3)_2SiCH_2CH_2Si(CH_3)_2Y$ Formula I can generally be written as D (YSiQ$_3$)$_2$ wherein Y is as previously defined and D is a connecting group chosen from:

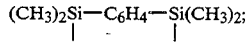

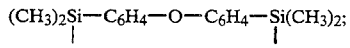

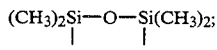

or

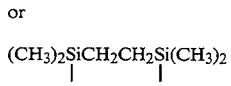

then the product D(YSiQ$_3$)$_2$ is formed by the reaction

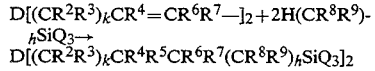    Eqn. 6A or

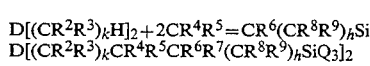    Eqn. 6B (j) when X is Y(CF$_2$)$_p$Y:

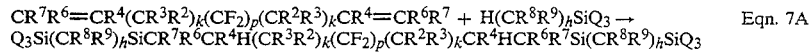    Eqn. 7A or

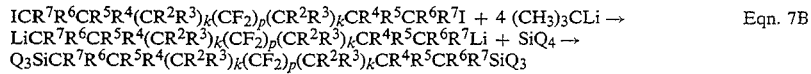    Eqn. 7B

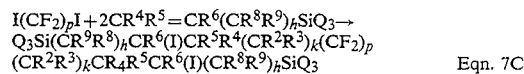    Eqn. 7C

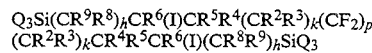

for k=0; p=4, 6 or 8; all R's=H:

can be converted to

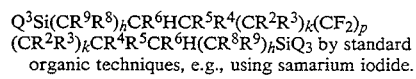 by standard organic techniques, e.g., using samarium iodide.

(k) when X is Y$_3$—Si—O—Si—Y$_3$:

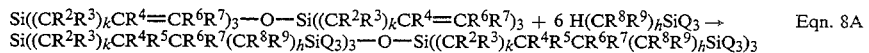    Eqn. 8A or

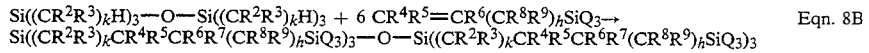    Eqn. 8B (l) when X is Y$_3$—Si—(CH$_2$)$_b$—Si—Y$^3$:

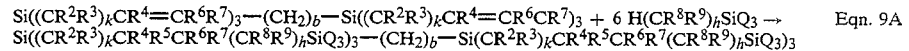    Eqn. 9A or

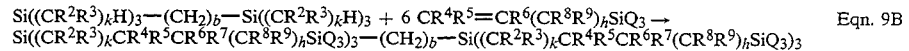    Eqn. 9B (m) when X is Y$_3$—Si—C$_6$H$_4$—Si—Y$_3$:

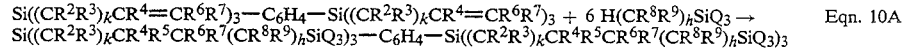    Eqn. 10A or

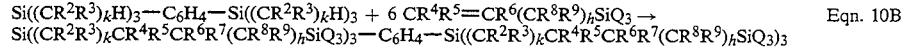    Eqn. 10B (n) when X is a substituted benzene structure of the type, as previously defined, which can be abbreviated C$_6$H$_{6-w}$(SiZ$_{3-a}$Y$_a$)$_w$:

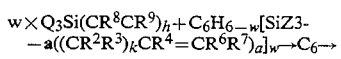

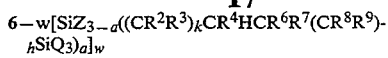

Eqn. 11A or

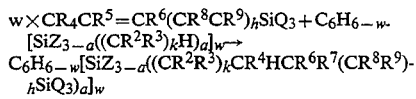

Eqn. 11B (o) when X is a substituted cyclohexane structure of the type, as previously defined, which can be abbreviated $C_6H_{12-w}(Y)_w$, wherein w is the number of substituents; then

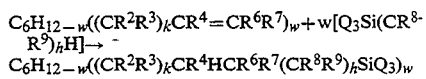

For convenience the reaction of Equations denoted A or B above is chosen depending upon the commercial availability of the starting reagents. In each set of equations where an A and B are presented, h=0 in Eqn. A and k=0 in Eqn. B. In (d), k=1 and h=0. Specific sources of reactants are listed hereinafter just prior to the Examples. The reactants are employed in a ratio such that the precursor containing the $SiQ_3$ group is employed in a molar excess of 10–50% to ensure completion of the hydrosilylation reaction. A transition metal catalyst such as platinum, or a free radical initiator is employed in an effective amount. Examples of suitable free radical initiators include VAZO® compounds available from E. I. du Pont de Nemours and Company, Wilmington, Del.

These reactions can be conducted at a temperature of from about 25° C. to about 100° C. Preferably the process is conducted at about 80° C. to about 100° C. The pressure employed is typically ambient, about 1 atm ($1.01 \times 10^5$ Pa). The reactions are carried out under an inert gas atmosphere, although use of an air atmosphere is not precluded. Reaction time is typically from about 4 hours to about 24 hours.

Use of solvent is not required in these reactions. Suitable solvents which may be employed are those capable of dissolving the reactants and which do not interfere with the reaction or generate unnecessary by-products. The desired product can be isolated by any means known to those skilled in the art. Preferably the desired product is isolated by removal of volatiles under reduced pressure.

NMR and K+IDS mass spectrometry have been used to characterize product purities. Typically, yields of completely reacted material exceed 85%, with the principal impurities being either reverse (Markovnikov) hydrosilylation or incompletely substituted material containing unreacted —CH=CH$_2$ groups. The catalyst can be removed, by filtering through silica gel or activated charcoal.

Synthesis of the star gel precursors wherein $X=Y(CF_2)_pY$ may also be afforded from a metallation reaction between an alpha-omega diiodoalkylperfluoroalkane, e.g., contacted with tert-butyl lithium, followed by reaction with Si(OEt)$_4$, as shown above in Equation 7B. Alternatively unsaturated trialkoxysilanes, or trihalosilanes can be inserted into the C-I bond of I(CF$_2$)$_p$I, followed by reduction of the C-I to C-H using standard organic reduction reagents as shown in Equation 7C. Examples of suitable reagents are zinc metal, tri-n-butyl tin hydride or samarium iodide.

Possible uses of star gel precursors of the present invention are as multifunctional cross-linkers for other sol-gel or polymeric systems, and very high surface area materials, i.e., aerogels, when dried via supercritical fluid media. Although the openness of a structure such as star gel precursor 1, Si[CH$_2$CH$_2$Si(OC$_2$H$_5$)$_3$]$_4$, suggests that the resulting glass would have open porosity and very high surface area, pore collapse can occur during drying via simple solvent evaporation when the network is sufficiently flexible leading to non-porous coatings or materials.

The present invention further comprises a process for the preparation of an inorganic/organic composition of formula (II). To form the composition of formula (II) of the present invention as defined above the alkoxysilane, acyloxysilane or halosilane groups of the star gel precursors of formula (I) or formula (III) as previously defined, are hydrolyzed with either water in the presence of a solvent and a catalyst, or one or more strong carboxylic acids, preferably formic acid, optionally in the presence of a solvent and condensed to form a continuous network of silicon-oxygen bonds. The silicon atoms bearing the hydrolyzed groups will be constituents of an infinite network structure via bonds to other silicon atoms through oxygen. Preferred star gel precursors of formula I or formula III for use in this process include those listed in Table I.

The present invention also further comprises a method for preparing compositions of glasses of formula II by combining two or more star gel precursors of the present invention of formula (I) or formula III with each other. If more than one compound of formula (I) or formula III, as defined above, is mixed, the star gel precursors may be represented as $X'(SiQ_3)_{n'}+X''(SiQ_3)_{n''}+\ldots$, wherein X' and X'' are different definitions of X and n' and n'' correspond to the definitions of X' and X'' respectively. The resulting inorganic/organic composition of formula (II), as defined above, will be $X(SiO_{1.5})_n$, where $X=\% X'+\% X''+\ldots$ and n=average of ($\% n'+\% n''+\ldots$). Star-derived glasses may also be produced in the presence of a dye such as Rhodamine G to yield an optically useful material.

The process of this invention has the desirable feature that no water need be added to the reactants initially and that the steady state water concentration during reaction can be quite small. One of the benefits of this feature is that clear gels can be made readily without a need to use a water-miscible solvent to obtain a homogeneous medium. While water is necessary for hydrolysis, a sufficient amount is formed by reaction of strong carboxylic acid with alcohol produced by hydrolysis and by the metathesis reaction:

Also, any water which may be present as diluent in strong carboxylic acid can contribute to hydrolysis.

Strong carboxylic acid containing at most 20 mol % water is preferred for the process of this invention. The carboxylic acids should have a $pk_a$ value not higher than about 4.0 and contain 0 to 20 mole % water. Examples of strong carboxylic acids effective in this invention include formic acid, monochloroacetic acid, dichloroacetic acid, trifluoroacetic acid and hydroxyacetic acid. Formic acid is the preferred carboxylic acid. After the star gel precursor is mixed with water in the presence of a solvent and a catalyst, or the strong carboxylic acid optionally in the presence of a solvent, the mixture is maintained at a temperature within the range of about 0°–100° C. at ambient pressure. The star gel is finally isolated via removal of liquid byproducts and unreacted starting materials to yield a glass.

When the star gel precursors of formula (I) or formula (III) are hydrolyzed with water in the presence of a solvent and a catalyst, suitable solvents comprise co-solvents for water and the star gel precursor of formula (I) or formula (III) or are miscible with water with an affinity for the star gel precursor of formula (I) or formula (III), e.g., alcohols, tetrahydrofuran, and acetonitrile. Suitable catalysts comprise Bronsted acids or weak bases where pH <9, e.g., hydrogen fluoride, sodium fluoride, sulfuric acid, acetic acid and ammonium hydroxide.

Those glasses of formula (II) prepared by drying the gels of formula (II) wherein the X component corresponds to a linear or cyclosiloxane show the greatest flexibility. This flexibility provides a more compliant network structure. The compliance incorporated into the network allows faster drying rates and imparts toughness to the resultant glasses prepared from gels of formula (II).

Star gel precursor 1, $Si[CH_2CH_2Si(OC_2H_5)_3]_4$, star gel precursor 2,

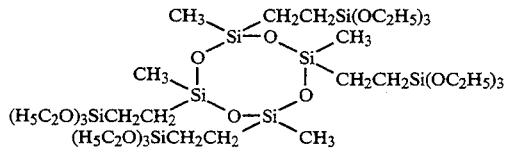

and star gel precursor 3, $Si[OSi(CH_3)_2CH_2CH_2Si(OC_2H_5)_3]_4$, in Table 1 are readily soluble in tetrahydrofuran and mixtures of that solvent with water or formic acid. The latter, formic acid, has been developed as a highly effective hydrolyric and condensation agent for tetraalkoxysilanes. Several star gel precursors, e.g., 3, can be added directly to formic acid to give a dispersion which rapidly clarifies as the molecule begins to react and silanol groups are generated. Gelation rates with formic acid can be extremely fast in the absence of solvent. Star gel precursor 3, $Si[OSi(CH_3)_2CH_2CH_2Si(OC_2H_5)_3]_4$ forms a gel with a 20-fold molar excess of HCOOH in 6 minutes. The use of a H-bonding acceptor solvent such as tetrahydrofuran can attenuate the gelation rate up to several orders of magnitude. A less reactive solvent such as methylene chloride will give a more rapid gelation rate than a hydrogen bonding solvent. Pure star gel precursors have long shelf life. Hydrolyric reagent and optional solvent and catalyst if water is used are added to initiate the reaction. Gels are clear except for the coloration imparted by any residual catalyst. They may be dried into monolithic glassy solids at rates at least five times those which lead to fracture of conventional gels of the same dimensions. Thick films of these glasses can be easily dried without any observed cracking upon drying. In this manner films that are five times thicker than those derived from sol-gel silica can be made crack free.

Dried samples of glass of formula (II) derived from star gel precursors 1, 2 and 3 as defined above and in Table I, do not show evidence of open porosity when submerged under water. Adsorption isotherm measurements using nitrogen at 77° K. also indicated no detectable surface-connected porosity for a sample of the glass derived from star gel precursor 1, $Si[CH_2CH_2Si(OC_2H_5)_3]_4$.

Impact resistance was examined by dropping a 150 g pestle from various heights onto pieces of star-derived and conventional sol-gel glasses of comparable size. The star glasses were able to sustain impacts which invariably fractured their conventional counterparts.

The new classes of compositions of formula (II), in addition to those cited above, are useful as abrasion resistant materials, impact resistant glasses, microporous glasses, interlayer dielectrics for electronic devices, adhesives for glass and other materials, and barrier coatings. Star gel precursors of formula (I), are useful as crosslinking agents for some functionalized organic polymers, coupling agents, or modifiers for alkoxysilane derived sol-gel glasses, other metal alkoxide derived sol-gel glasses, and other star-gel glasses.

The present invention further comprises a method for modifying conventional sol-gel glasses as defined in Brinker, C. J., et al., Sol Gel Science, Academic Press, San Diego, Calif. (1990), to increase drying rates and lower brittleness comprising combining a precursor of the present invention of formula (I) or of formula (III) with a conventional sol-gel system based on tetraalkoxysilanes or other metal alkoxides; mixing in water with a solvent and a catalyst, or a carboxylic acid, preferably formic acid, optionally in the presence of a solvent; and drying. The known tetralkoxysilane or other metal alkoxide is combined with a star gel precursor of the present invention, preferably the star gel precursors include those found in Table I, to generate a homogenous solution. These components are miscible and useable in any proportion, e.g., from 0.1:99.9 to 99.9:to 0.1. Water with a solvent and a catalyst, or a carboxylic acid, preferably formic acid, optionally in the presence of a solvent, is then added with stirring at ambient temperature and pressure to induce gelation. The resulting gel is then dried. Typically drying is at atmospheric pressure and at a temperature of from about 20° C. to 150° C. Vacuum up to $10^{-5}$ torr may be employed. The gelation rate of $Si(OC_2H_5)_4$ by formic acid can be profoundly influenced by addition of small amounts of a star gel precursor of formula (I) or formula (III). A mixture of $Si(OC_2H_5)_4$ and HCOOH at a molar ratio of 1:3 normally requires 18 hours to gel. Substitution of 10 mole % star gel precursor 1, $Si[CH_2CH_2Si(OC_2H_5)_3]_4$, for Si(OC$_2$H$_5$)$_4$ led to a gelation time of 8 minutes under comparable conditions. Other sol-gel glasses from inorganic alkoxides, for example alkoxides of Al, Zr, V, B, Ti, Nb, Ge, Sn, Ga, In, Cu and Pb can be modified in a similar fashion.

A method of coating a substrate is also provided by the present invention comprising reacting a star gel precursor of formula (I) or formula (III), preferably including those in Table I, with water in the presence of a solvent and a catalyst, or a carboxylic acid, such as formic acid, optionally in the presence of a solvent, such as tetrahydrofuran, dipping the substrate in the resulting mixture, removing the coated substrate from the mixture and drying the coating. Thus the substrate is dipped into the mixture containing the star gel precursor prior to gelation, and after gelation and drying the substrate is coated with an inorganic/organic composition of formula (II). The star gel precursor of formula (I) or formula (III) or inorganic/organic composition of formula (II) may also be used as an adhesive by coating a substrate and placing another substrate on top of it and applying pressure, optionally accompanied by or followed by heat. Suitable substrates comprise glass, metal and plastic.

In the examples which follow all star numbers refer to the star gel precursors listed in Table I. All reactions were carried out in a Vacuum Atmospheres Co. dry box under nitrogen. Commercial reagents were distilled prior to use. Triethoxysilane, tetravinylsilane, vinyltriethoxysilane, 1,3,5,7-tetramethylcyclotetrasilane, 1,3,5,7-tetravinyltetramethylcyclotetrasilane, 1,1,3,3-tetravinyldimethyldisiloxane, tetraallyloxysilane, tetrakis(dimethylsiloxy)silane, p-bis(dimethylsilyl)benzene, bis[p-dimethylsilyl)phenyl]ether, 1,1,3,3-tetramethyldisiloxane, 1,1,4,4-tetramethyldisilethylene, pentamethylcyclopentasiloxane, methyltris(dimethylsiloxy)silane, chlorodimethylvinylsilane, tetraethoxysilane and trichlorosilane were purchased from Huls America Inc., Piscataway, N.J. Allyltriethoxsilane; trimethoxysilane; triethoxysilane, 1,3,5-tribromobenzene; 1,2,4-trivinylcyclohexane and tert-butyllithium (1.7M in pentane) were purchased from Aldrich Chemical Col., Milwaukee, Wis. Tetraethoxysilane was purchased from Eastman Kodak, Rochester, N.Y. Platinum divinylsiloxane complex (3–3.5% Pt concentration in xylene, Huls PC072) was obtained from Huls America Inc. and diluted 5:1 by volume (toluene, Pt complex) prior to use. Cobalt carbonyl and P(OCH$_3$)$_3$ were obtained from E. I. du Pont de Nemours and Company. Toluene was reagent grade and purified by distillation from lithium aluminum hydride prior to use. Tetrallylsilane was synthesized by a modification of a published procedure (J. Organomet. Chem., 84(1975), pp. 199–299). 1,3,5-(CH$_2$=CH(CH$_3$)$_2$Si)$_3$C$_6$H$_3$ was synthesized by a modification of a published procedure using CH$_2$=CHCH$_3$)$_2$SICl instead of Si(OC$_2$H$_5$)$_4$ (Macromolecules, 24 (1991), pp. 6863–6866). The preparation of silicon alkoxides (Si-OR) from chlorosilanes (Si-Cl) and alcohol was accomplished according to known procedures (Organosilicon Compounds, C. Eaborn, Academic Press Inc., NY, 1960, pp. 288–311). Vinylpolyfluoroalkanes CH$_2$=CH(CF$_2$)$_p$CH=CH$_2$(p=6, 10), CH$_2$=CH(CH$_2$)$_4$(CF$_2$)$_{10}$(CH$_2$)$_4$CH=CH$_2$, and ICH$_2$CH$_2$(CF$_2$)$_6$CH$_2$I were obtained pure from E. I. du Pont de Nemours and Company, Wilmington, Del. Normal purification of the star gel precursors involved flash chromotography on silica gel using hexane as the elutant unless otherwise noted. The silica gel column was treated with Si(OCH$_3$)$_4$ before addition of the star gel precursors. The K+IDS mass specroscopy experiments were performed on a Finnigan 4615B GC/MS quadrupole mass spectrometer (San Jose, Calif.). An electron impact source configuration operating at 200° C. and a source pressure of $1.0 \times 10^{-6}$ Torr was used. The mass spectrometer was scanned at a rate of about 1000 Daltons/second. All K+IDS mass spectral peaks are recorded as sum of the ion plus potassium (M+39). Proton and carbon NMR were determined in deuterobenzene solvent on a GE model QE-300 instrument. Elemental analyses were performed by Oneida Research Services Inc., One Halsey Road, Whitesboro, N.Y.

EXAMPLES

EXAMPLE 1

Synthesis and Characterization of Star 1, Si[CH$_2$CH$_2$Si(OC$_2$H$_5$)$_3$]$_4$ To a mixture of 55.596 g (0.338 mol) of triethoxysilane and 10 drops (approximately 0.3 ml) of Pt catalyst was added 5.219 g (0.038 mol) of tetravinylsilane dropwise over a period of 1 hour. The temperature of the reaction mixture was controlled so as to not exceed 35° C. After the addition, the solution was heated to 90° C. for 6 hours, then cooled and stirred at room temperature for 18 hours. The excess triethoxysilane was removed in vacuo at 60° C. Proton NMR of the product showed some residual vinyl groups. An additional 11.842 g (0.0720 mol) of triethoxysilane and 4 drops of Pt catalyst was added to the crude mixture and heated to 90° C. for 6 hours. Cooling to room temperature and workup as described above yielded 26.75 g (88%) of a clear liquid determined to be mostly Si[CH$_2$CH$_2$Si(OC$_2$H$_5$)$_3$]$_4$. Purity was found to be 91% by K+IDS mass spectroscopy and >75% by supercritical fluid chromatography (SFC). K+IDS MS (m/e) 831 (M+39, 100%), 667 (H$_2$C=CH) Si[CH$_2$CH$_2$Si(OC$_2$H$_5$)$_3$]$_3$+39, 8.6%) . 13C NMR(C$_6$D$_6$) 3,57 (SiCH$_2$), 4.05 (SiCH$_2$), 19.0 (CH$_3$), 59.0 (SiOCH$_2$). Small amounts of —SiCH (CH$_3$)Si(OC$_2$H$_5$)$_3$ groups due to Markovnikov (or reverse-hydrosilation) addition (1.0, 9.0 ppm) were observed. Anal: Calcd for C$_{32}$H$_{76}$Si$_5$O$_{12}$ C, 48.45; H, 9.65; Si, 17.70. Found: C, 47.72; H, 9.59; Si, 17.37.

EXAMPLE 2

Synthesis and Characterization of Star 2, ((CH$_3$)$_4$(C$_2$H$_5$O)$_3$SiCH$_2$CH$_2$)$_4$(SiO)$_4$ To a stirred mixture of 2.85 g (0.0083 mol) of ((CH$_3$)(CH$_2$=CH) SiO)$_4$ and 8.15 g (0.0496 mol) of triethoxysilane was added 14 drops (ca 0.4 ml) of Pt catalyst. The resulting solution was heated to 100° C. for 2.5 hours, cooled and stirred at room temperature for 18 hours. The excess HSi(OC$_2$H$_5$)$_3$ was removed in vacuo and workup as described previously yielded a clear liquid identified as $((CH_3)((C_2H_5O)_3SiCH_2CH_2)SiO)_4$. Impurities were mainly the di- and tri-substituted products as noted by K+IDS MS. $^{13}C$ NMR($C_6D_6$) −0.901 (($CH_3$)Si), 2.98 ($SiCH_2$), 9.30 ($SiCH_2$), 19.01 ($CH_3$), 58.99 ($SiOCH_2$). K+IDS MS (m/e) 1039 (M+39, 100 %), 875 (3-arm product+39, 52%), 711 (2-arm product+39, 3%). Anal. Calcd for $C_{36}H_{88}Si_8O_{16}$: C, 43.16; H, 8.85. Found: C, 42.12; H, 8.65.

EXAMPLE 3

Synthesis and Characterization of Star 3, $Si(OSi(CH_3)_2CH_2CH_2Si(OC_2H_5)_3)_4$ To a stirred mixture of 3.039 g (0.0092 mol) of $Si(OSi(CH_3)_2H)_4$ and 10.024 g (0.05278 mol) of vinyltriethoxysilane was added 14 drops (ca 0.4 ml) of Pt catalyst. The resulting solution was stirred for 2 hours, heated to 90° C. for 4 hours, cooled and stirred at room temperature for 18 hours. The excess $(CH_2=CH)Si(OC_2H_5)_3$ was removed in vacuo and workup as described previously yielded a clear liquid identified as $Si(OSi(CH_3)_2CH_2CH_2Si(OC_2H_5)_3)_4$. Impurity levels were on the order of 5% or less. $^{13}C$ NMR($C_6D_6$) −0.43 (($CH_3$)Si), 3.19 ($SiCH_2$), 10.17 ($SiCH_2$), 19.09 ($CH_3$), 58.86 ($SiOCH_2$). K+IDS MS (m/e) 1128 (M+39, 100%). Anal. Calcd for $C_{40}H_{100}Si_9O_{16}$: C, 44.08; H, 9.25; Si, 23.19. Found: C, 44.66; H, 9.31; Si, 22.46.

EXAMPLE 4

Synthesis and Characterization of Star 4, $Si(OCH_2CH_2CH_2Si(OC_2H_5)_3)_4$

A mixture of 3.12 g (0.0118 mol) of $Si(OCH_2CH=CH_2)_4$, 11.028 g (0.0671 mol) of $HSi(OC_2H_5)_3$ and 14 drops of Pt catalyst was stirred at 25° C. for 2 hours and then heated to 90° C. for 4 hours. The solution was cooled, and the volatiles removed in vacuo. Workup as described above yielded 6.49 g of a clear liquid identified as $Si(OCH_2CH_2CH_2Si(OC_2H_5)_3)_4$. $^{13}C$ NMR ($C_6D_6$) 7.39 ($SiCH_2$), 18.97 ($CH_3$), 26.93 ($CH_2$), 58.89 (SiO $\underline{CH_2}CH_3$), 66.55 ($SiCH_2$). K+IDS MS (m/e) 952 (M+39, 100%). Anal. Calcd for $C_{36}H_{84}Si_5O_{16}$: C, 47.37; H, 9.27; Si, 15.37. Found: C, 46.32; H, 9.10; Si, 16.06.

EXAMPLE 5

Synthesis and Characterization of Star 5, $((C_2H_5O)_3SiCH_2CH_2)_2(CH_3)SiOSi(CH_3)(CH_2CH_2Si(OC_2H_5)_3)_2$ To a stirred solution of 2.12 g (0.0101 mol) of $((CH_2=CH)_2(CH_3)Si)_2O$ and 14 drops of Pt catalyst was added 7.93 g (0.0483 mol) of $HSi(OC_2H_5)_3$ via a syringe over a period of 1 hour. The mixture was heated to 90° C. for 4 hours, then cooled to room temperature. The volatiles were removed in vacuo and the reaction product was worked up as described above yielding 3.80 g of a liquid identified as $((C_2H_5O)_3SiCH_2CH_2)_2(CH_3)SiOSi(CH_3)(CH_2CH_2Si(OC_2H_5)_3)_2$. Small amounts of impurities (<5%) were noted in the NMR corresponding to the tri-substituted product. $^{13}C$ NMR($C_6D_6$) −2.01 ($CH_3Si$), 3.27 ($SiCH_2$), 8.32 ($SiCH_2$), 19.02 ($CH_3$), 58.92 ($SiOCH_2$). K+IDS MS (m/e) 905 (M+39, 100%), 743 (3-arm product+39, 25%). Anal. Calcd for $C_{34}H_{82}Si_6O_{13}$: C, 47.07; H, 9.53; Si, 19.43. Found: C, 45.69; H, 9.40; Si, 19.40.

EXAMPLE 6

Synthesis and Characterization of Star 6, $(C_2H_5O)_3SiCH_2CH_2(CH_3)_2SiC_6H_4Si(CH_3)_2CH_2CH_2Si(OC_2H_5)_3$ A mixture of 2.91 g (0.0150 mol) of $H(CH_3)_2C_6H_4(CH_3)_2H$, 10.03 g (0.0527 mol) of $(CH_2=CH)Si(OC_2H_5)_3$ and 14 drops of Pt catalyst was stirred at 25° C. for 2 hours and then heated to 90° C. for hours. The solution was cooled, and the volatiles removed in vacuo. Workup as described above yielded 11.6 g of a liquid identified as Star 6. $^{13}C$ NMR($C_6D_6$) −3.11 ($SiCH_3$), 3.85 ($SiCH_2$), 7.80 ($SiCH_2$), 19.0 ($CH_3$), 26.93 ($CH_2$), 58.9 (SiO $\underline{CH_2}$ $CH_3$), 133.7, 136.6, 140.2 (aromatics). K+IDS MS (m/e) 614 (M+39, 100%). Anal. Calcd for $C_{26}H_{54}Si_4O_6$: C, 54.31; H, 9.46. Found: C, 53.53; H, 9.40.

EXAMPLE 7

Synthesis and Characterization of Star 7, $(C_2H_5O)_3SiCH_2CH_2(CH_3)_2SiC_6H_4OC_6H_4Si(CH_3)_2CH_2CH_2Si(OC_2H_5)_3$ A mixture of 4.32 g (0.0151 mol) of $(H(CH_3)_2C_6H_4)_2O$, 10.02 g (0.0526 mol) of $(CH_2=CH)Si(OC_2H_5)_3$ and 14 drops of Pt catalyst was stirred at 25° C. for 2 hours and then heated to 90° C. for 4 hours. The solution was cooled, and the volatiles removed in vacuo. The resulting brown liquid was stirred over activated charcoal and filtered yielding 3.59 g of a clear liquid identified as Star 7. $^{13}C$ NMR($C_6D_6$) −2.93 ($SiCH_3$), 3.89 ($SiCH_2$), 7.99 ($SiCH_2$), 19.06 ($CH_3$), 58.94 (SiO $\underline{CH_2}$ $CH_3$), 119.2, 133.8, 136.0, 158.9 (aromatics). Anal. Calcd for $C_{32}H_{58}Si_4O_7$: C, 57.61; H, 8.76. Found: C, 57.03; H, 8.77.

EXAMPLE 8

Synthesis and Characterization of Star 8, $(C_2H_5O)_3SiCH_2CH_2(CH_3)_2SiOSi(CH_3)_2CH_2CH_2Si(OC_2H_5)_3$ A solution consisting of 2.01 g (0.0150 mol) of $(H(CH_3)_2Si)_2O$, 10.01 g (0.0526 mol) of $(CH_2=CH)Si(OC_2H_5)_3$ and 14 drops of Pt catalyst was stirred at 25° C. for hours and then heated to 90° C. for 4 hours. The solution was cooled, and the volatiles removed in vacuo. Workup as described above yielded 10.67 g of a clear liquid identified as Star 8. Small impurities (about were noted in the NMR spectra. $^{13}C$ NMR($C_6D_6$) 0.22 ($SiCH_3$), 3.24 ($SiCH_2$), 10.41 ($SiCH_2$), 18.88 ($CH_3$), 58.95 (SiO $\underline{CH_2}$ $CH_3$). K+IDS MS (m/e) 553 (M+39, 45%)

EXAMPLE 9

Synthesis and Characterization of Star 9, $(C_2H_5O)_3SiCH_2CH_2(CH_3)_2SiCH_2CH_2Si(CH_3)_2CH_2CH_2Si(OC_2H_5)_3$ To a mixture consisting of 10.50 g (0.0552 mol) of $(CH_2=CH)Si(OC_2H_5)_3$ and 14 drops of Pt catalyst was added 3.72 g (0.0254 mol) of $(H(CH_3)_2SiCH_2)_2$ over a 30 min period. The temperature was kept around 35° C. during the addition. The mixture was then heated to 90° C. for 6 hours. After cooling, the volatiles removed in vacuo yielding 10.39 g of a clear liquid identified as Star 9. Some minor impurities were noted in the NMR spectra. $^{13}C$ NMR $(C_6D_6)$ −3.89 $(SiCH_3)$, 3.82 $(SiCH_2)$, 6.71 $(SiCH_2)$, 7.46 $(SiCH_2)$, 19.07 $(CH_3)$, 58.95 (SiO $\underline{CH_2}$ $CH_3$). K+IDS MS (m/e) 565 (M+39, 100%). Anal. Calcd for $C_{22}H_{54}Si_4O_6$: C, 50.14; H, 10.33. Found: C, 50.10; H, 10.35.

The reaction was performed in a manner similar to Star 9 using 10.03 g (0.0527 mol) of $(CH_2=CH)Si(OC_2H_5)_3$, 2.89 g (0.0096 mol) of $((CH_3)(H)SiO)_5$ and 14 drops of Pt catalyst. Workup yielded 8.66 g of a clear liquid identified as Star 10. $^{13}C$ NMR $(C_6D_6)$ −0.75 $(SiCH_3)$, 3.12 $(SiCH_2)$, 9.48 $(SiCH_2)$, 19.05 $(CH_3)$, 58.95 (SiO $\underline{CH_2}$ $CH_3$). K+IDS MS (m/e) 1290 (M+39, 100%). Anal. Calcd for $C_{45}H_{110}Si_{10}O_{20}$: C, 43.16; H, 8.85. Found: C, 43.15; H, 8.79.

EXAMPLE 11

Synthesis and Characterization of Star 12, $((CH_3)_4(C_2H_5O)_3SiCH_2CH_2CH_2)_4(SiO)_4$ The reaction was performed in a manner similar to Star 9 using 10.04 g (0.0491 mol) of $(CH_2=CHCH_2)Si(OC_2H_5)_3$, 2.32 g (0.0097 mol) of $((CH_3)(H)SiO)_4$ and 14 drops of Pt catalyst. Workup yielded 7.74 g of a liquid identified as Star 12. $^{13}C$ NMR$(C_6D_6)$, 0.131 $(SiCH_3)$, 15.57 $(SiCH_2)$, 17.64 $(SiCH_2)$, 19.03 $(CH_3)$, 22.07 $(CH_2)$, 58.79 (SiO $\underline{CH_2}$ $CH_3$). K+IDS MS (m/e) 1095 (M+39, 100%). Anal. Calcd for $C_{40}H_{96}Si_8O_{16}$: C, 45.42; H, 9.15. Found: C, 46.35; H, 9.26.

EXAMPLE 12

Synthesis and Characterization of Star 13, $((CH_3)_5(C_2H_5O)_3SiCH_2CH_2CH_2)_5(SiO)_5$ The reaction was performed in a manner similar to Star 9 using 8.49 g (0.0416 tool) of $(CH_2=CHCH_2)Si(OC_2H_5)_3$, 2.45 g (0.0082 mol) of $((CH_3)(H)SiO)_5$ and 14 drops of Pt catalyst. Workup yielded 5.94 g of a liquid identified as Star 12. $^{13}C$ NMR$(C_6D_6)$ 0.269 $(SiCH_3)$, 15.74 $(SiCH_2)$, 17.79 $(SiCH_2)$, 19.04 $(CH_3)$, 22.40 $(CH_2)$, 58.83 (SiO $\underline{CH_2}$ $CH_3$). K+IDS MS (m/e) 1359 (M+39, 100%). Anal. Calcd for $C_{50}H_{120}Si_{10}O_{20}$: C, 45.42; H, 9.15. Found: C, 46.41; H, 9.23.

EXAMPLE 13

Synthesis and Characterization of Star 14, $Si(OSi(CH_3)_2CH_2CH_2CH_2Si(OC_2H_5)_3)_4$ To a stirred mixture of 10.04 g (0.0491 mol) of allyltriethoxysilane and 14 drops (ca 0.4 ml) of Pt catalyst was added 3.17 g (0.0096 mol) of $Si(OSi(CH_3)_2H)_4$ over a period of 1 hour. The resulting solution was heated to 90° C. for 4 hours, cooled and stirred at room temperature for 18 hours. The excess $(CH_2=CHCH_2)Si(OC_2H_5)_3$ was removed in vacuo and workup as described previously yielded 8.84 g of a liquid identified as $Si(OSi(CH_3)_2CH_2CH_2CH_2Si(OC_2H_5)_3)_4$. $^{13}C$ NMR$(C_6D_6)$ −0.14 $((CH_3)Si)$, 15.04 $(SiCH_2)$, 16.74 $(SiCH_2)$, 17.80 $(CH_3)$, 22.13 $(-CH_2-)$, 58.86 $(SiOCH_2)$. K+IDS MS (m/e) 1183 (M+39, 100%). Anal. Calcd for $C_{44}H_{108}Si_5O_{16}$: C, 46.11; H, 9.50. Found: C, 46.28; H, 9.55.

EXAMPLE 14

Synthesis and Characterization of Star 15, $(C_2H_5O)_3SiCH_2CH_2CH_2(CH_3)_2SiC_6H_4Si(CH_3)_2CH_2CH_2CH_2Si(OC_2H_5)_3$ To a stirred mixture of 9.56 g (0.0468 mol) of allyltriethoxysilane and 14 drops (ca 0.4 ml) of Pt catalyst was added 2.94 g (0.0151 mol) of $H(CH_3)_2SiC_6H_4Si(CH_3)_2H$ over a period of 30 min. The resulting solution was heated to 90° C. for 4 hours, cooled and stirred at room temperature for 18 hours. The excess $(CH_2=CHCH_2)Si(OC_2H_5)_3$ was removed in vacuo and workup as described previously yielded 9.63 g of a liquid identified as Star 15. $^{13}C$ NMR $(C_6D_6)$ −2.43 $((CH_3)Si)$, 15.96 $(SiCH_2)$, 18.53 $(SiCH_2)$, 19.00 $(CH_3)$, 20.42 $(-CH_2-)$, 58.82 $(SiOCH_2)$. K+IDS MS (m/e) 641 (M+39, 100%).

EXAMPLE 15

Synthesis and Characterization of Star 17, $(CH_3)Si(OSi(CH_3)_2CH_2CH_2Si(OC_2H_5)_3)_3$ A stirred mixture of 10.01 g (0.0609 mol) of triethoxysilane, 14 drops (ca 0.4 ml) of Pt catalyst and 3.35 g (0.0123 mol) of $(CH_3)Si(OSi(CH_3)_2CH=CH_2)_3$ was stirred at 25° C. for 2 hours and then heated to 90° C. for 4 hours, cooled and stirred at room temperature for 18 hours. The excess $HSi(OC_2H_5)_3$ was removed in vacuo yielding 15.46 g of a clear liquid identified as $(CH_3)Si(OSi(CH_3)_2CH_2CH_2Si(OC_2H_5)_3)_3$. $^{13}C$ NMR $(C_6D_6)$ 0.11 $((CH_3)Si)$, 3.16 $(SiCH_2)$, 10.30 $(SiCH_2)$, 18.82 $(CH_3)$, 58.76 $(SiOCH_2)$. Anal. Calcd for $C_{31}H_{78}Si_7O_{12}$: C, 44.35; H, 9.36. Found: C, 44.99; H, 9.46

EXAMPLE 16

Synthesis and Characterization of Star 18, $Si(CH_2CH_2Si(OCH_3)_3)_4$

To a stirred mixture of 2.21 g (0.0162 tool) of tetravinylsilane and 7 drops (ca 0.4 ml) of Pt catalyst was added 12.016 g (0.0096 mol) of trimethoxysilane over a period of 1 hour. The resulting solution was heated to 90° C. for 4 hours, cooled and stirred at room temperature for 18 hours. The excess $HSi[O(CH_3)]_3$ was removed in vacuo yielding 9.78 g of a liquid identified as $Si(CH_2CH_2Si(OCH_3)_3)_4$. Column chromatography of the Star product resulted in partial hydrolysis of Si-CCH3 groups. Some Markovnikov addition products, similar to those observed in Star 1, were also seen in the NMR. $^{13}C$ NMR $(C_6D_6)$ 2.69 $(SiCH_2)$, 3.34 $(SiCH_2)$, 50.8 (SiOCH$_3$). K+IDS MS (m/e) 663 (M+39, 90%), 617 ((CH$_3$)$_2$O+39, 100%).

EXAMPLE 17

Gel from Star 1 with water/ethanol 1.868 g Star 1 was dissolved in 2.42 g anhydrous ethanol to give a homogeneous solution. 0.510 g of water containing 0.040 g 0.1N HCl was added to this solution over a period of two minutes with moderate stirring. The ratio of water to Si(OR) groups was 1.00. The solution remained clear and formed a clear gel after 23 hours. The wet gel was dried initially at room temperature and atmospheric pressure, then at a temperature of 120° C.-and a pressure of 10$^{-5}$ torr. The dry gel was pulverized and subjected to pore size analysis by the BET method adsorption analysis using nitrogen at −196° C. in accordance with ASTM standard C$_{1069}$-86. The sample did not show a significant weight gain due to nitrogen adsorption after 4 hours. Small pieces of the dried gel were submerged in water and observed under a microscope. No evidence of fracture or gas liberation was observed. Taken together, these observations indicate the sample did not possess open porosity.

EXAMPLE 18

Gel from Star 3 with HCOOH 1.562 g Star 3 was added to 1.86 g 96% formic acid with stirring. The mixture formed a clear solution after several seconds. The ratio of acid to Si(OR) groups was 2.26. The solution was transferred into a polyethylene vial and allowed to stand at room temperature. The sample formed a transparent gel after 13 min. The contents of the vial were allowed to dry via slow evaporation of the liquid component of the gel. The material was fully dried after two weeks and had formed an intact smooth right cylinder which was translucent. The dried gel remained intact after impact from a 150 g pestle dropped from a heights of 2–3 cm. Comparably sized pieces of conventional sol-gel glasses were consistently fractured from the same impact exposure.

EXAMPLE 19

Attenuation of Gelation Rate for Star 3 with Tetrahydrofuran 1.183 g Star 3 was dissolved in 3.20 g tetrahydrofuran (THF). 0.526 g 96% formic acid was added to above solution with stirring. The ratio of acid to Si(OR) groups was 0.842. The solution was transferred into a fluoropolymer vial and allowed to stand at room temperature. The sample formed a transparent gel after 19 days.

EXAMPLE 20

Dip and Flow coats from Star 1 HCOOH/Tetrahydrofuran 3.36 g Star 1 was combined with 12.37 g tetrahydrofuran and 2.35 g formic acid per Example 4. The ratio of acid to Si(OR) groups was 0.96. The solution (which gelled in four hours) was used to prepare coatings on glass slides via dip and flow coating techniques. Coatings made three hours after the reactants were mixed were transparent and crack-free. The flow coating was shown by surface profilometry to be 2.5 micrometers in thickness; the dip coating was 0.5 micrometers in thickness.

EXAMPLE 21

Gel from Star 1 with tetraethoxysilane in HCOOH; Gel rate enhancement 0.865 Star 1 was combined with 2.04 g tetraethoxysilane to give a homogeneous solution which was added to 1.53 g HCOOH with stirring. The resultant solution gelled in 8.3 minutes. The Star was 10 mole % of the total silanes present. The ratio of acid to silanes was 2.93. At the same molar ratio of HCOOH/silane, pure tetraethoxysilane requires ca. 18 hours for gelation.

EXAMPLE 22

High Surface Area Gel from Star 1 with tetraethoxysilane 1.064 g Star 1 combined with 2.492 g tetraethoxysilane to give a homogeneous solution which was added to 3.161 g HCOOH with stirring. The resultant solution gelled in 1.5 minutes. The Star was 10 mole % of the total silanes present. At the same molar ratio of HCOOH/silane (4.96), pure tetraethoxysilane requires ca. 2 hours for gelation. The wet gel was dried under vacuum at 60° C. within minutes of its preparation, then at a temperature of 120° C. and a pressure of 10$^{-5}$ torr. The dry gel was then subjected to porosity analysis per the procedure in Example 17. The surface area was determined to be 629 m$^2$/g, with an average pore size of approximately 2.0 nanometers. The surface area value is higher than those observed by this procedure for gels made from tetraethoxysilane without the star gel precursor.

EXAMPLE 23

Gel from star 10 with HCOOH/methylene chloride 1.92 g of star gel precursor 10 was dissolved in 4.05 g reagent grade methylene chloride to give a homogeneous solution. 0.785 g of 96% formic acid was added dropwise to this solution over a period of one minute with moderate stirring. The ratio of acid to Si(OR) groups was 0.71. The resultant solution remained clear and later formed a clear gel on standing overnight. Several drops of the solution were placed between two 25×75 mm glass microscope slides so as to form a thin continuous layer between the slides. After several hours, the slides were firmly bonded together and could not be separated or moved relative to each other by moderate amounts of force, illustrating the adhesive nature of the gel.

EXAMPLE 24

Synthesis and Characterization of Star 11

Si(CH$_2$CH$_2$CH$_2$Si(OC$_2$H$_5$)$_3$)$_4$ {(a); m=0; k=0; h=0; all R's=H}

To a stirred solution of 5.28 g (0.0321 mol) of HSi(OC$_2$H$_5$)$_3$ and 5 drops of Pt catalyst solution in 20 mL of hexane was added 0.626 g (0.0033 mol) of Si(CH$_2$CH=CH$_2$)$_4$ over a two minute period. The mixture was refluxed for 1 hr and stirred at 25° C. for 60 hr. The unreacted volatiles were removed in vacuo, and the crude mixture was worked up as described previously yielding 1.78 g (64%) of Si(CH$_2$CH$_2$CH$_2$Si(OC$_2$H$_5$)$_3$)$_4$. $^{13}$C NMR(C$_6$D$_6$) 16.46, 17.89, 18.65 (SiCH$_2$), 19.05 (CH$_3$), 58.83 (SiOCH$_2$CH$_3$). K$^+$IDS MS (m/e) (M+39, 100%).

EXAMPLE 25

Synthesis and Characterization of Star 16 (C$_2$H$_5$O)$_3$SiCH$_2$CH$_2$(CF$_2$)$_6$CH$_2$CH$_2$Si(OC$_2$H$_5$)$_3$ {(j); p=6; k=0, h=0, all R's=H}

To a stirred mixture of 0.041 g (0.120 mmol) of Co$_2$(CO)$_8$, 0.029 g (0.234 mmol) of P(OCH$_3$)$_3$ in 1 mL of toluene was added 2.48 g (6.503 mmol) of CH$_2$=CH(CF$_2$)$_6$CH=CH$_2$ and 5.34 g (32.5 mmol) of HSi(OC$_2$H$_5$)$_3$. The mixture was stirred at room temperature for 4 days and an extra 3.22 g of HSi(OC$_2$H$_5$)$_3$ was added to ensure completion of the reaction. After stirring for 11 days the solution was heated at 60° C. for 6 hr; and stirred at room temperature for another 7 days until there was no remaining vinyl groups observed in the NMR. Standard workup provided 5.19 g of a dark brown solution. The remaining color was removed by the addition of activated charcoal. The ratio of CH$_2$=CH(CF$_2$)$_6$CH$_2$CH$_2$Si(OC$_2$H$_5$)$_3$ to (C$_2$H$_5$O)$_3$SiCH$_2$CH$_2$(CF$_2$)$_6$CH$_2$CH$_2$Si(OC$_2$H$_5$)$_3$ in the product mixture was found to be 74% to 26%. K$^+$IDS MS (m/e) 557 (monosubstituted, M+39, 100%), 721 (M+39, 65%). GC/MS (CI-isobutane) exact mass for C$_{16}$H$_{22}$O$_3$SiF$_{12}$+H, calcd m/e 519. 1225, found m/e 519.1263, exact mass for C$_{22}$H$_{38}$O$_6$Si$_2$F$_{12}$+H, calcd m/e 683.2093, found m/e 683.2144.

EXAMPLE 26

Synthesis and Characterization of Cl$_3$SiCH$_2$CH$_2$(CF$_2$)$_n$CH$_2$CH$_2$SiCl$_3$(n=6, 10) {(j); p=6, 10; k=0, h=0, all R's=H; Q=Cl}

To a 10 mL pressure vessel was added 1.28 g (3.36 mmol) of CH$_2$=CH(CF$_2$)$_6$CH=CH$_2$, 1.32 mL (13.08 mmol) of HSiCl$_3$ and one drop of Pt catalyst. The reaction vessel was sealed and heated at 100° C. for 48 hr. The vessel was cooled, and the excess HSiCl$_3$ was removed in vacuo leaving a 1.622 g (77% yield) of a white solid. GC analysis showed that the solid is a single compound. 1H NMR (C$_6$D$_6$) 1.05 (m, 2H, SiCH$_2$), 1.98 (m, 2H, SiCH$_2$). The preparation of Cl$_3$SiCH$_2$CH$_2$(CF$_2$)$_{10}$CH$_2$CH$_2$SiCl$_3$ was performed in a similar manner using 3.66 g (6.66 mmol) of CH$_2$=CH(CF$_2$)$_6$CH=CH$_2$, 2.71 g (20.02 mmol) of HSiCl$_3$. A temperature of 120° C. for 48 hr was needed to ensure complete reaction. Workup yielded 1.63 g (30%) of Cl$_3$SiCH$_2$CH$_2$(CF$_2$)$_{10}$CH$_2$CH$_2$SiCl$_3$ as the only product. 1H NMR(C$_6$D$_6$) 1.02 (m, 2H, SiCH$_2$), 1.91 (m, 2H, SiCH$_2$). The conversion of Cl$_3$SiCH$_2$CH$_2$(CF$_2$)$_n$CH$_2$CH$_2$SiCl$_3$ to (C$_2$H$_5$O)$_3$SiCH$_2$CH$_2$(CF$_2$)$_n$CH$_2$CH$_2$Si(OC$_2$H$_5$)$_3$ can be accomplished by known literature methods using ethanol.

EXAMPLE 27

Synthesis and Characterization of Star 16 (C$_2$H$_5$O)$_3$SiCH$_2$CH$_2$(CF$_2$)$_6$CH$_2$CH$_2$Si(OC$_2$H$_5$)$_3$ {(j); p=6, k=0, h=0, all R's=H}

A stirred solution containing 0.259 g (0.424 mmol) of [ICH$_2$CH$_2$(CF$_2$)$_3$]$_2$ dissolved in 10 mL of ether was cooled to −78° C. To this was added 1.01 mL (1.71 mmol) of tert-butyl lithium. The resulting mixture was stirred for 1.5 h and 1.90 mL (8.518 mmol) of Si(OC$_2$H$_5$)$_4$ was added. The mixture was warmed to room temperature and stirred for 90 hr. The volatiles were removed in vacuo yielding 0.054 g (18%) of a brown residue. GC/MS (CI-isobutane) shows the residue is mainly (C$_2$H$_5$O)$_3$SiCH$_2$CH$_2$(CF$_2$)$_6$CH$_2$CH$_2$Si(OC$_2$H$_5$)$_3$ (calcd m/e/ 683.2156, found (C$_2$H$_5$O)$_3$SiCH$_2$CH$_2$(CF$_2$)$_6$CH$_2$Si(OC$_2$H$_5$)$_3$ (But).

EXAMPLE 28

Synthesis and Characterization of Star 21 (C$_2$H$_5$O)$_3$(CH$_2$)$_6$(CF$_2$)$_{10}$(CH$_2$)$_6$Si(OC$_2$H$_5$)$_3$ {(j); p=10, k=4, h=0, all R's=H}

A solution consisting of 5.00 g (7.51 mmol) of {CH$_2$=CH(CH$_2$)$_4$(CF$_2$)$_5$]$_2$, 5.55 g (33.8 mmol) of HSi(OC$_2$H$_5$)$_3$, 10 drops of Pt catalyst in 20 mL of toluene was heated at 90° C. for 6 hr, and stirred at room temperature for 10 hr. The volatiles were removed in vacuo and normal workup provided 6.45 g (86%) of (C$_2$H$_5$O)$_3$Si(CH$_2$)$_6$(CF$_2$)$_{10}$(CH$_2$)$_6$Si(OC$_2$H$_5$)$_3$ as an off-white waxy solid. $^{13}$C NMR(C$_6$D$_6$) 11.50, 20.71, 23.53, 29.27, 33.12 (CH$_2$), 31.58 (t, CH$_2$CF$_2$, 2J(C-F)=22 hz), 18.99 (SiOCH$_2$CH$_3$), 58.91 (SiOCH$_2$CH$_3$). K$^+$IDS MS (m/e) 1033 (M+39, 100%).

EXAMPLE 29

Synthesis and Characterization of Star 19 1,3,5-((C$_2$H$_5$O)$_3$SiCH$_2$CH$_2$(CH$_3$)$_2$Si)$_3$C$_6$H$_3$ {Z=CH$_3$; k=0, h=0, all R's=H}

To 3.01 g (9.12 mmol) of 1,3,5-((C$_2$H$_5$O)$_3$SiCH$_2$CH$_2$(CH$_3$)$_2$Si)$_3$C$_6$H$_3$ and eight drops of Pt catalyst was added 5.54 g (33.7 mmol) of HSi(OC$_2$H$_5$)$_3$. The resulting mixture was heated to 90° C. for 6 hr and stirred at room temperature for 16 hr. Standard workup provided 5.83 g (78%) of 1,3,5-((C$_2$H$_5$O)$_3$SiCH$_2$CH$_2$(CH$_3$)$_2$Si)$_3$C$_6$H$_3$ as the sole product. $^{13}$C NMR(C$_6$D$_6$) −2.91 (CH$_3$Si), 4.05 (CH$_2$), 7.99 (CH$_2$), 19.03 (SiOCH$_2$CH$_3$), 58.97 (SiOCH$_2$CH$_3$), 137.96, 140.32 (aromatic). K$^+$IDS MS (m/e) 861 (M+39, 100%).

EXAMPLE. 30

Synthesis and Characterization of Star 20 1,2,4-((C$_2$H$_5$O)$_3$SiCH$_2$CH$_2$)$_3$C$_6$H$_3$ {k=0, h=0, all R's=H}

A mixture containing 3.206 g (0.0198 mol) of 1,2,4-trivinylcyclohexane, 26.32 g (0.160 mol) of HSi(OC$_2$H$_5$)$_3$ and 10 drops of Pt catalyst was stirred at room temperature. Oxygen was bubbled through the solution for 5 min., and then the solution was heated to reflux for 7 hr, cooled and stirred at room temperature for 16 hr. Standard workup provided 11.68 g (90%) of 1,2,4-((C$_2$H$_5$O)$_3$SiCH$_2$CH$_2$)$_3$C$_6$H$_3$ as a clear liquid. $^{13}$C NMR(C$_6$D$_6$) 5.98 to 42.72 (many peaks, CH$_2$, CH), 18.18 (SiOCH$_2$CH$_3$), 17.97 (disubst, SiOCH$_2$CH$_3$), 58.17 (SiOCH$_2$CH$_3$), 58.15 (disubst, SiOCH$_2$CH$_3$). K$^+$IDS MS (m/e) 693 (M+39, 100%). A small amount of disubstituted product, (CH$_2$=CH)((C$_2$H$_5$O)$_3$-

SiCH₂CH₂)₂C₆H₉, was also observed 529 (M+39, 26%).

EXAMPLE 31

Formation of Very Low Surface Energy Glass

Approximately 0.35 g (0.35 mmol) Star 21 (C₂H₅O)₃Si(CH₂)₆(CF²)₁₀(CH₂)₆Si(OC₂H₅)₃, was dissolved in 1.00 g reagent grade tetrahydrofuran to give a homogeneous solution. Approximately 0.25 g (5.43 mmol) of 96% formic acid was added dropwise to this solution over a period of one minute with moderate stirring. The resultant solution remained clear and formed a clear yellow gel on standing overnight. The yellow color is believed due to residual platinum catalyst from the synthesis of the Star. The gel was dried over the course of several days at room temperature into a clear yellow glassy disk weighing 0.278 g. No evidence for open porosity in the glass was obtained when it was submerged in fluids which wet the surface well.

The surface energy of the glass was assessed by measuring contact angles for several different liquids via the sessile drop method (A. W. Anderson, Physical Chemistry of Surfaces, 4th ed., Wiley-Interscience, NY, 1982, pp. 341-342). After these measurements, the sample was exposed to the silylating agent bistrimethylsilyl acetamide (a 10% solution by weight in acetonitrile) for 15 min. at room temperature so as to convert residual high energy silanol (Si-OH) surface groups into Si—O—SiMe₃ groups. The contact angle measurements were then repeated. The very high contact angles for water and methylene iodide indicate a highly hydrophobic low energy surface, especially after the silylation reaction. The surface energy was calculated to be 15.2 mN/meter, substantially less than that for poly(tetrafluoroethylene) [Teflon ®]. The surface energy was calculated according to the equation $$\cos \theta = -1 + 2(\gamma_1^d \gamma_s^d)^{\frac{1}{2}}/\gamma_1^d$$

where the superscript d refers to the dispersive component of the liquid or solid free energies g, and is listed in Table II. The equation, which is quite accurate in predicting contact angles of both polar and non-polar liquids on polymers, is based on the assumptions that the reversible work of adhesion can be approximated by its dispersive component, and that the solid/vapor free energy is negligible. See B. Sauer, J. Adhesion Sci. Tech., 6, 955 (1992) for details.

TABLE II

| Fluoroglass Sample Surface Energy Data | | | |
|---|---|---|---|
| | As Generated | After Silylation | PTFE* |
| Contact angle water (advancing) | 90° | 123° | 110° |
| Contact angle CH₂I₂ | Not Measured | 90° | 83° |
| Contact angle n-hexadecane | 0 | 11° | 40° |
| Surface energy mN/meter | ca. 30 | 15.2 | 23.9 |

*Poly(tetrafluoroethylene)

What is claimed is:

1. An inorganic/organic composition of the idealized empirical formula (II):

$$X(SiO_{1.5})_n \quad (II)$$

wherein
   n is an integer greater than or equal to 2; and
   X is at least one flexible organic link selected from the group consisting of:
   (a) R¹ₘSiY₄₋ₘ;
   (b) ring structures

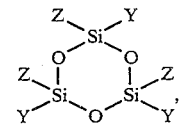
IIa

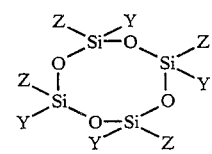
IIb and

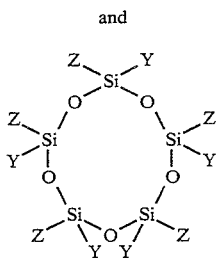
IIc (c) R¹ₘSi(OSi(CH₃)₂Y)₄₋ₘ;
   (d) R¹ₘSi(OY)₄₋ₘ;
   (e) CH₃SiY₂—O—SiY₂CH₃;
   (f) Y(CH₃)₂Si—C₆H₄—Si(CH₃)₂Y;
   (g) O[—C₆H₄—Si(CH₃)₂Y]₂;
   (h) O[Si(CH₃)₂Y]₂;
   (i) Y(CH₃)₂SiCH₂—CH₂Si(CH₃)₂Y;
   (j) Y₃SiOSiY₃;
   (k) Y₃Si(CH₂)ᵦSiY₃;
   (l) Y₃SiC₆H₄SiY₃;
   (m) substituted benzene selected from the group consisting of:
     (i) C₆H₃(SiZ₃₋ₐYₐ)₃;
     (ii) C₆H₂(SiZ₃₋ₐYₐ)₄;
     (iii) C₆H(SiZ₃₋ₐYₐ)₅; and
     (iv) C₆(SiZ₃₋ₐYₐ)₆; and
   (n) substituted cyclohexane selected from the group consisting of:
     (i) 1,2-C₆H₁₀(Y)₂; 1,3-C₆H₁₀(Y)₂; 1,4-C₆H₁₀(Y)₂;
     (ii) 1,2,4-C₆H₉(Y)₃; 1,2,3-C₆H₉(Y)₃; 1,3,5-C₆H₉(Y)₃;
     (iii) 1,2,3,4-C₆H₈(Y)₄; 1,2,4,5-C₆H₈(Y)₄; 1,2,3,5-C₆H₈(Y)₄;
     (iv) 1,2,3,4,5-C₆H₇(Y)₅; and
     (v) C₆H₆(Y)₆;

wherein:
   Z is an alkyl group of 1 to 4 carbon atoms, 3,3,3-trifluoropropyl, aralkyl, or aryl;
   Y is (CR²R³)ₖCR⁴R⁵CR⁶R⁷(CR⁸R⁹)ₕ—;
   R¹ is alkyl of 1 to about 8 carbon atoms or aryl;
   R² to R⁹ are each independently hydrogen, alkyl of 1 to about 8 carbon atoms or aryl, provided that at least one of R⁴ to R⁷ is hydrogen;
   m is 0, 1 or 2;
   k and h are each independently an integer from 0 to 10, provided that at least one of k or h is zero;

a is 1, 2 or 3;
p is an even integer from 4 to 10; and
b is an integer from 1 to 10.

2. A process for the preparation of the composition of formula (II)

$$X(SiO_{1.5})_n \quad (II)$$

wherein
n is an integer greater than or equal to 2; and
X is at least one flexible organic link selected from the group consisting of:
(a) $R^1_m SiY_{4-m}$;
(b) ring structures

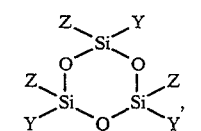
IIa

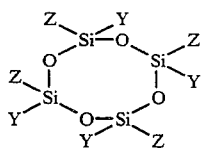
IIb and

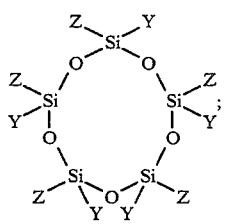
IIc (c) $R^1_m Si(OSi(CH_3)_2Y)_{4-m}$;
(d) $R^1_m Si(OY)_{4-m}$;
(e) $CH_3SiY_2$—O—$SiY_2CH_3$;
(f) $Y(CH_3)_2Si$—$C_6H_4$—$Si(CH_3)_2Y$;
(g) $O[$—$C_6H_4$—$Si(CH_3)_2Y]_2$;
(h) $O[Si(CH_3)_2Y]_2$;
(i) $Y(CH_3)_2SiCH_2$—$CH_2Si(CH_3)_2Y$;
(j) $Y(CF_2)_pY$, provided that when p is 6, Y is other than ethylene;
(k) $Y_3SiOSiY_3$;
(l) $Y_3Si(CH_2)_bSiY_3$;
(m) $Y_3SiC_6H_4SiY_3$;
(n) substituted benzene selected from the group consisting of:
 (i) $C_6H_3(SiZ_{3-a}Y_a)_3$;
 (ii) $C_6H_2(SiZ_{3-a}Y_a)_4$;
 (iii) $C_6H(SiZ_{3-a}Y_a)_5$; and
 (iv) $C_6(SiZ_{3-a}Y_a)_6$; and
(o) substituted cyclohexane selected from the group consisting of:
 (i) 1,2-$C_6H_{10}(Y)_2$; 1,3-$C_6H_{10}(Y)_2$; 1,4-$C_6H_{10}(Y)_2$;
 (ii) 1,2,4-$C_6H_9(Y)_3$; 1,2,3-$C_6H_9(Y)_3$; 1,3,5-$C_6H_9(Y)_3$;
 (iii) 1,2,3,4-$C_6H_8(Y)_4$; 1,2,4,5-$C_6H_8(Y)_4$; 1,2,3,5-$C_6H_8(Y)_4$;
 (iv) 1,2,3,4,5-$C_6H_7(Y)_5$; and
 (v) $C_6H_6(Y)_6$;
wherein:

Z is an alkyl group of 1 to 4 carbon atoms, 3,3,3-trifluoropropyl, aralkyl, or aryl;
Y is $(CR^2R^3)_k CR^4R^5 CR^6R^7 (CR^8R^9)_h$—;
$R^1$ is alkyl of 1 to about 8 carbon atoms or aryl;
$R^2$ to $R^9$ are each independently hydrogen, alkyl of 1 to about 8 carbon atoms or aryl, provided that at least one of $R^4$ to $R^7$ is hydrogen;
m is 0, 1 or 2;
k and h are each independently an integer from 0 to 10, provided that at least one of k or h is zero;
a is 1, 2 or 3;
p is an even integer from 4 to 10; and
b is an integer from 1 to 10 comprising:
(A) mixing at least one compound of formula (III):

$$X(SiQ_3)_n \quad (III)$$

wherein:
Q is alkoxy of 1 to about 8 carbon atoms, acyloxy of 1 to about 8 carbon atoms;
n is an integer greater than or equal to 2; and
X is at least one flexible organic link selected from the group consisting of:
(a) $R^1_m SiY_{4-m}$;
(b) ring structures

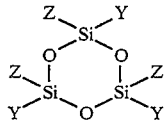
IIIa

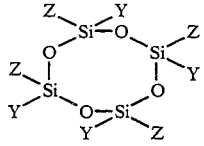
IIIb and

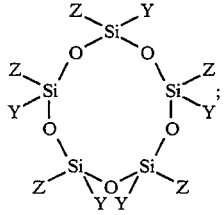
IIIc (c) $R^1_m Si(OSi(CH_3)_2Y)_{4-m}$;
(d) $R^1_m Si(OY)_{4-m}$;
(e) $CH_3SiY_2$—O—$SiY_2CH_3$;
(f) $Y(CH_3)_2Si$—$C_6H_4$—$Si(CH_3)_2Y$;
(g) $O[$—$C_6H_4$—$Si(CH_3)_2Y]_2$;
(h) $O[Si(CH_3)_2Y]_2$;
(i) $Y(CH_3)_2SiCH_2$—$CH_2Si(CH_3)_2Y$;
(j) $Y(CF_2)_pY$, provided that when p is 6, Y is other than ethylene;
(k) $Y_3SiOSiY_3$;
(l) $Y_3Si(CH_2)_bSiY_3$;
(m) $Y_3SiC_6H_4SiY_3$;
(n) substituted benzene selected from the group consisting of:
 (i) $C_6H_3(SiZ_{3-a}Y_a)_3$;
 (ii) $C_6H_2(SiZ_{3-a}Y_a)_4$;
 (iii) $C_6H(SiZ_{3-a}Y_a)_5$; and
 (iv) $C_6(SiZ_{3-a}Y_a)_6$; and (o) substituted cyclohexane selected from the group consisting of:
  (i) 1,2-C$_6$H$_{10}$(Y)$_2$; 1,3-C$_6$H$_{10}$(Y)$_2$; 1,4-C$_6$H$_{10}$(Y)$_2$
  (ii) 1,2,4-C$_6$H$_9$(Y)$_3$; 1,2,3-C$_6$H$_9$(Y)$_3$; 1,3,5-C$_6$H$_9$(Y)$_3$;
  (iii) 1,2,3,4-C$_6$H$_8$(Y)$_4$; 1,2,4,5-C$_6$H$_8$(Y)$_4$; 1,2,3,5-C$_6$H$_8$(Y)$_4$;
  (iv) 1,2,3,4,5-C$_6$H$_7$(Y)$_5$; and
  (v) C$_6$H$_6$(Y)$_6$;

wherein:
Z is an alkyl group of 1 to 4 carbon atoms, 3,3,3-trifluoropropyl, aralkyl, or aryl;
Y is (CR$^2$R$^3$)$_k$CR$^4$R$^5$CR$^6$R$^7$(CR$^8$R$^9$)$_h$—;
R$^1$ is alkyl of 1 to about 8 carbon atoms or aryl;
R$^2$ to R$^9$ are each independently hydrogen, alkyl of 1 to about 8 carbon atoms or aryl, provided that at least one of R$^4$ to R$^7$ is hydrogen;
m is 0, 1 or 2;
k and h are each independently an integer from 0 to 10, provided that at least one of k or h is zero;
a is 1, 2 or 3;
p is an even integer from 4 to 10; and
b is an integer from 1 to 10, in the presence of water a solvent and a catalyst, or in the presence of at least one carboxylic acid having a maximum pKa value about 4.0 and containing from 0 to 20 mole % water and an optional solvent;

(B) maintaining the mixture resulting from step (A) at a temperature within the range of about 0°–100° C.; and (C) isolating the resulting inorganic/organic composition of formula (II).

3. A method for modifying a sol-gel glass to generate a sol-gel glass that can tolerate increased drying rates and shows lower brittleness comprising:

(A) combining a star gel precursor of formula (III):

X(SiQ$_3$)$_n$      (III)

wherein:
Q is alkoxy of 1 to about 8 carbon atoms, acyloxy of 1 to about 8 carbon atoms, of halogen;
n is an integer greater than or equal to 2; and
X is at least one flexible organic link selected from the group consisting
  (a) R$^1_m$SiY$_{4-m}$;
  (b) ring structures

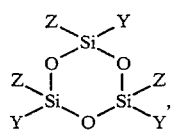

IIIa

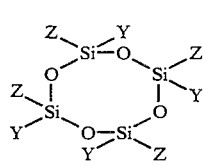

IIIb and

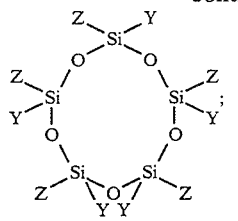

IIIc (c) R$^1_m$Si(OSi(CH$_3$)$_2$)$_{4-m}$;
(d) R$^1_m$Si(OY)$_{4-m}$;
(e) CH$_3$SiY$_2$—O—SiY$_2$CH$_3$;
(f) Y(CH$_3$)$_2$Si—C$_6$H$_4$—Si(CH$_3$)$_2$Y;
(g) O[—C$_6$H$_4$—Si(CH$_5$)$_2$Y]$_2$;
(h) O[Si(CH$_3$)$_2$Y]$_2$;
(i) Y(CH$_3$)$_2$SiCH$_2$—CH$_2$Si(CH$_3$)$_2$Y;
(j) Y(CF$_2$)$_p$Y;
(k) Y$_3$SiOSiY$_3$;
(l) Y$_3$Si(CH$_2$)$_b$SiY$_3$;
(m) Y$_3$SiC$_6$H$_4$SiY$_3$;
(n) substituted benzene selected from the group consisting of:
  (i) C$_6$H$_3$(SiZ$_{3-a}$Y$_a$)$_3$;
  (ii) C$_6$H$_2$(SiZ$_{3-a}$Y$_a$)$_4$;
  (iii) C$_6$H(SiZ$_{3-a}$Y$_a$)$_5$; and
  (iv) C$_6$(SiZ$_{3-a}$Y$_a$)$_6$; and
(o) substituted cyclohexane selected from the group consisting of:
  (i) 1,2-C$_6$H$_{10}$(Y)$_2$; 1,3-C$_6$H$_{10}$(Y)$_2$; 1,4-C$_6$H$_{10}$(Y)$_2$
  (ii) 1,2,4-C$_6$H$_9$(Y)$_3$; 1,1,3-C$_6$H$_9$(Y)$_3$; 1,3,5-C$_6$H$_9$(Y)$_3$;
  (iii) 1,2,3,4-C$_6$H$_8$(Y)$_4$; 1,2,4,5-C$_6$H$_8$(Y)$_4$; 1,2,3,5-C$_6$H$_8$(Y)$_4$;
  (iv) 1,2,3,4,5-C$_6$H$_7$(Y)$_5$; and
  (v) C$_6$H$_6$(Y)$_6$;

wherein:
Z is an alkyl group of 1 to 4 carbon atoms, 3,3,3-trifluoropropyl, aralkyl, or aryl;
Y is (CR$^2$R$^3$)$_k$CR$^4$R$^5$CR$^6$R$^7$(CR$^8$R$^9$)$_h$—;
R$^1$ is alkyl of 1 to about 8 carbon atoms or aryl;
R$^2$ to R$^9$ are each independently hydrogen, alkyl of 1 to about 8 carbon atoms or aryl, provided that at least one of R$^4$ to R$^7$ is hydrogen;
m is 0, I or 2;
k and h are each independently an integer from 0 to 10, provided that least one of k or h is zero;
a is 1, 2 or 3;
p is an even integer from 4 to 10; and
b is an integer from i to 10;

with an inorganic alkoxide sol-gel precursor;

(B) mixing in water with a solvent and a catalyst, or mixing a carboxylic acid having a maximum pk$_a$ value of about 4 optionally in the presence of a solvent; and (C) drying.

4. A method for coating a substrate comprising reacting the star gel precursor of formula (III):

X(SiQ$_3$)$_n$      (III)

wherein:
Q is alkoxy of 1 to about 8 carbon atoms, acyloxy of 1 to about 8 carbon atoms, or halogen;
n is an integer greater than or equal to 2; and X is at least one flexible organic link selected from the group consisting of:
(a) $R^1{}_m Si(Y)_{4-m}$;
(b) ring structures

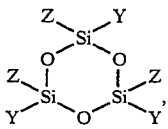  IIIa

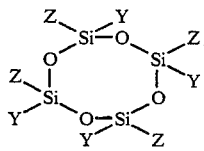  IIIb and

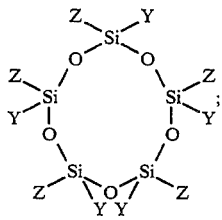  IIIc (c) $R^1{}_m Si(OSi(CH_3)_2 Y)_{4-m}$,
(d) $R^1{}_m Si(OY)_{4-m}$,
(e) $CH_3 SiY_2-O-SiY_2 CH_3$;
(f) $Y(CH_3)_2 Si-C_6 H_4-Si(CH_3)_2 Y$;
(g) $O[-C_5 H_4-Si(CH_3)_2 Y]_2$;
(h) $O[Si(CH_3)_2 Y]_2$;
(i) $Y(CH_3)_2 SiCH_2-CH_2 Si(CH_3)_2 Y$;
(j) $Y(CF_2)_p Y$;
(k) $Y_3 SiOSiY_3$;
(l) $Y_3 Si(CH_2)_b SiY_3$;
(m) $Y_3 SiC_6 H_4 SiY_3$;
(n) substituted benzene selected from the group consisting of:
  (i) $C_6 H_3 (SiZ_{3-a} Y_a)_3$;
  (ii) $C_6 H_2 (SiZ_{3-a} Y_a)_4$;
  (iii) $C_6 H(SiZ_{3-a} Y_a)_5$; and
  (iv) $C_6 (SiZ_{3-a} Y_a)_6$; and
(o) substituted cyclohexane selected from the group consisting of:
  (i) 1,2-$C_6 H_{10}(Y)_2$; 1,3-$C_6 H_{10}(Y)_2$; 1,4-$C_6 H_{10}(Y)_2$
  (ii) 1,2,4-$C_6 H_9(Y)_3$; 1,2,3-$C_6 H_9(Y)_3$; 1,3,5-$C_6 H_9(Y)_3$;
  (iii) 1,2,3,4-$C_6 H_8(Y)_4$; 1,2,4,5-$C_6 H_8(Y)_4$; 1,2,3,5-$C_6 H_8(Y)_4$;
  (iv) 1,2,3,4,5-$C_6 H_7(Y)_5$; and
  (v) $C_6 H_6(Y)_6$;
wherein,
Z is an alkyl group of 1 to 4 carbon atoms, 3,3,3-trifluoropropyl, aralkyl or aryl;
Y is $(CR^2 R^3)_k CR^4 R^5 CR^6 R^7 (CR^8 R^9)_h-$;
$R^1$ is alkyl of 1 to about 8 carbon atoms or aryl;
$R^2$ to $R^9$ are each independently hydrogen, alkyl of 1 to about 8 carbon atoms or aryl, provided that it least one of $R^4$ to $R^7$ is hydrogen;
m is 0, 1 or 2;
X and h are each independently an integer from 0 to 10, provided that at least one of k or h is zero; and
a is 1, 2 or 3;
p is an even integer from 4 to 10; and
b is an integer from 1 to 10;

in the presence of water, a solvent and a catalyst, or in the presence of a strong carboxylic acid having a maximum $pk_a$ value of about 4, optionally in the presence of a solvent; dipping the substrate in the resulting mixture; removing the coated Substrate from the mixture and drying the coating to generate a substrate coated with a composition of formula II $X(SiO_{1.5})_n$ (II)

wherein
n is an integer greater than or equal to 2; and
X is at least one flexible organic link selected from the group consisting of:
(a) $R^1{}_m SiY_{4-m}$;
(b) ring structures

 IIa

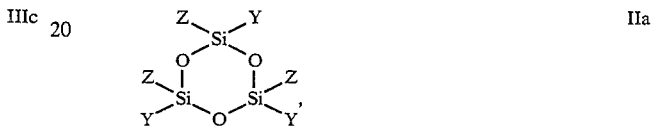 IIb and

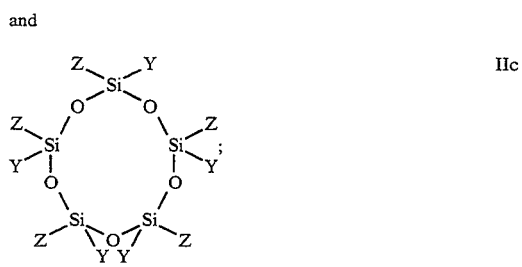 IIc (c) $R^1{}_m Si(OSi(CH_5)_2 Y)_{4-m}$,
(d) $R^1{}_m Si(OY)_{4-m}$,
(e) $CH_3 SiY_2-O-SiY_2 CH_3$;
(f) $Y(CH_3)_2 Si-C_6 H_4-Si(CH_3)_2 Y$;
(g) $O[-C_6 H_4-Si(CH_3)_2 Y]_2$;
(h) $O[Si(CH_5)_2 Y]_2$;
(i) $Y(CH_3)_2 SiCH_2-CH_2 Si(CH_3)_2 Y$;
(j) $Y(CF_2)_p Y$, provided that when p is 6, Y is other than ethylene;
(k) $Y_3 SiOSiY_3$;
(l) $Y_3 Si(CH_2)_b SiY_3$;
(m) $Y_3 SiC_6 H_4 SiY_3$;
(n) substituted benzene selected from the group consisting of:
  (i) $C_6 H_3 (SiZ_{3-a} Y_a)_3$;
  (ii) $C_6 H_2 (SiZ_{3-a} Y_a)_4$;
  (iii) $C_6 H(SiZ_{3-a} Y_a)$; 5; and
(o) substituted cyclohexane selected from the group consisting of:
  (i) 1,2-$C_6 H_{10}(Y)_2$; 1,3-$C_6 H_{10}(Y)_2$; 1,4-$C_6 H_{10}(Y)_2$;
  (ii) 1,2,4-$C_6 H_9(Y)_3$; 1,2,3-$C_6 H_9(Y)_3$; 1,3,5-$C_6 H_9(Y)_3$;
  (iii) 1,2,3,4-$C_6 H_8(Y)_4$; 1,2,4,5-$C_6 H_8(Y)_4$; 1,2,3,5-$C_6 H_8(Y)_4$;
  (iv) 1,2,3,4,5-$C_6 H_7(Y)_5$; and
  (v) $C_6 H_6(Y)_6$;
wherein:

Z is an alkyl group of 1 to 4 carbon atoms, 3,3,3-trifluoropropyl, aralkyl, or aryl;

Y is $(CR^2R^3)_k CR^4R^5CR^6R^7(CR^8R^9)_h-$;

$R^1$ is alkyl of 1 to about 8 carbon atoms or aryl;

$R^2$ to $R^9$ are each independently hydrogen, alkyl of 1 to about 8 carbon atoms or aryl, provided that at least one of $R^4$ to $R^7$ is hydrogen;

m is 0, 1 or 2;

k and h are each independently an integer from 0 to 10, provided that at least one of k or h is zero;

a is 1, 2 or 3;

p is an even integer from 4 to 10; and b is an integer from 1 to 10.

5. An inorganic/organic gel of the idealized empirical formula:

$$X(SiO_{1.5})_n$$

wherein:

n is an integer greater than or equal to 2; and

X is at least one flexible organic link of the formula:

$$Y(CF_2)_p Y,$$

wherein:

Y is $(CR^2R^3)_k CR^4R^5CR^6R^7(CR^8R^9)_h-$;

$R^2$ to $R^9$ are each independently hydrogen, alkyl or 1 to about 8 carbon atoms or aryl, provided that at least one of $R^4$ to $R^7$ is hydrogen;

k and h are each independently an integer from 4 to 10, provided that at least one of k or h is zero; and p is an even integer from 4 to 10.

* * * * *

UNITED STATES PATENT AND TRADEMARK OFFICE
CERTIFICATE OF CORRECTION

PATENT NO. : 5,378,790
DATED : January 3, 1995
INVENTOR(S) : Michalczyk et al.

It is certified that error appears in the above-identified patent and that said Letters Patent is hereby corrected as shown below:

<u>Col. 10, line 1</u>: Change "(iii) $C_6{}^H(SiZ_{3-a}Y_a)_5$; and" to --(iii) $C_6H(SiZ_{3-a}Y_a)_5$; and --;

<u>Col. 13, line 28</u>: Change "$C_1$" to --Cl--;

<u>Col. 16</u>, Change "(1) when X is $Y_3$-Si-$(CH_2)_b$-Si-$Y^3$:" to --(1) when X is $Y_3$-Si-$(CH_2)_b$-Si-$Y_3$--;

<u>Col. 16, line 67</u>: Change "w x $Q_3Si(CR^8CR^9)_h$ + $C_6H_{6-w}[SiZ3$-" to --w x $Q_3Si(CR^8CR^9)_hH$ + $C_6H_{6-w}[SiZ_3$- --;

<u>Col. 17, line 1</u>: Change "$6-w[SiZ_{3-a}$ $((CR^2R^3)_kCR^4HCR^6R^7(CR^8R^9)$-" to --$H_{6-w}[SiZ_{3-a}((CR^2R^3)_kCR^4HCR^6R^7(CR^8R^9)$- --;

<u>Col. 17, line 5</u>: Change "w x $CR_4CR^5=CR^6(CR^8CR^9)_hSiQ_3$ + $C_6H_{6-w}$-" to --w x $CR^4CR^5=CR^6(CR^8CR^9)_hSiQ_3$ + $C_6H_{6-w}$- --;

<u>Col. 19, line 52</u>: Change "hydrolyric" to --hydrolytic--;

<u>Col. 21, line 61</u>: Change "$CH_2=CHCH_3)_2SICl$" to --$CH_2=CHCH_3)_2SiCl$--;

<u>Col. 24, line 17</u>: Before "hours." insert --4--;

<u>Col. 24, line 59</u>: Before "hours" insert --2--;

<u>Col. 24, line 64</u>: Before "were noted" insert -- 5%)--;

<u>Col. 26, line 65</u>: Change "$CCH_3$" to --$OCH_3$--;

<u>Col. 30, line 37-38</u>: Change "1,3,5-$((C_2H_5O)_3SiCH_2CH_2(CH_3)_2Si)_3C_6H_3$" to --1,3,5-$(CH_2=CH(CH_3)_2Si)_3C_6H_3$--;

<u>Col. 35, line 47</u>: Change "of halogen" to --or halogen--;

<u>Col. 37, line 32</u>: Change "(g) $O[-C_5H_4-Si(CH_3)_2Y]_2$;" to --(g) $O[-C_6H_4-Si(CH_3)_2Y]_2$;--;

<u>Col. 37, line 64</u>: Change "X and h" to --k and h--;

UNITED STATES PATENT AND TRADEMARK OFFICE
CERTIFICATE OF CORRECTION

PATENT NO. : 5,378,790
DATED : January 3, 1995
INVENTOR(S) : Michalczyk et al.

It is certified that error appears in the above-identified patent and that said Letters Patent is hereby corrected as shown below:

<u>Col. 38, line 42</u>: Change "(c)$R^1_m Si(OSi(CH_5)_2 Y)_{4-m}$," to --(c) $R^1_m Si(OSi(CH_3)_2 Y)_{4-m}$,--; and <u>Col. 38, line 47</u>: Change "(h) $O[Si(CH_5)_2 Y]_2$;" to --(h) $O[Si(CH_3)_2 Y]_2$;--;

Signed and Sealed this

Seventeenth Day of December, 1996

Attest:

BRUCE LEHMAN

*Attesting Officer*    Commissioner of Patents and Trademarks